United States Patent
Kesteleyn et al.

(10) Patent No.: US 7,126,015 B2
(45) Date of Patent: Oct. 24, 2006

(54) METHOD FOR THE PREPARATION OF HEXAHYDRO-FURO-[2,3-B]FURAN-3-OL

(75) Inventors: Bart Rudolf Romanie Kesteleyn, Berlare (BE); Dominique Louis Nestor Surleraux, Machelen (BE); Peter Jan Leonard Mario Quaedflieg, Waalre (NL)

(73) Assignee: Tibotec Pharmaceuticals Ltd., Dublin (IE)

( * ) Notice: Subject to any disclaimer, the term of this patent is extended or adjusted under 35 U.S.C. 154(b) by 288 days.

(21) Appl. No.: 10/489,059

(22) PCT Filed: Sep. 6, 2002

(86) PCT No.: PCT/EP02/10062

§ 371 (c)(1), (2), (4) Date: Mar. 9, 2004

(87) PCT Pub. No.: WO03/022853

PCT Pub. Date: Mar. 20, 2003

(65) Prior Publication Data

US 2004/0249175 A1  Dec. 9, 2004

(30) Foreign Application Priority Data

Sep. 10, 2001  (EP) ................... 01203416

(51) Int. Cl.
C07D 493/06  (2006.01)

(52) U.S. Cl. ..................................... 549/464

(58) Field of Classification Search ............... 549/464
See application file for complete search history.

(56) References Cited

FOREIGN PATENT DOCUMENTS

| WO | 94/26749 | * 11/1994 |
| WO | WO 95/06030 | 3/1995 |
| WO | WO 99/67417 | 12/1999 |
| WO | WO 01/25240 A1 | 4/2001 |

OTHER PUBLICATIONS

Schreiber et al., Tetrahed. Letter, (1986), vol. 27(23), pp. 2575-2578.*
Schreiber et al., Tetrahed. Letter, (1988), vol. 29(51), pp. 6689-6692.*
Arun K. Ghosh et al., Nonpeptidal $P_2$ Ligands for HIV Protease Inhibitors: Structure-Based Design, Synthesis, and Biological Evaluation, J. Med. Chem., 1996, 39, pp. 3278-3290.
M. Pezechk et al., A New Route to Perhydro- and Tetrahydro-Furo-2,3b Furans via Radical Cyclisation, Tetrahydron Letters, vol. 27, No. 32, pp. 3715-3718, 1986.
M. Uchiyama et al., Steroselective synthesis of optically active perhydrofuro[2,3-b]furan derivatives, Tetrahedron Letters 42 (2001) pp. 4653-4656.

* cited by examiner

*Primary Examiner*—Taofiq Solola
(74) *Attorney, Agent, or Firm*—Woodcock Washburn LLP

(57) ABSTRACT

The present invention relates to a method for the preparation of hexahydro-furo[2,3-b]furan-3-ol as well as novel intermediates for use in said method. More in particular the invention relates to a stereoselective method for the preparation of hexahydro-furo[2,3-b]furan-3-ol, and to a method amenable to industrial scaling up.

25 Claims, No Drawings

METHOD FOR THE PREPARATION OF HEXAHYDRO-FURO-[2,3-B]FURAN-3-OL

CROSS REFERENCE TO RELATED APPLICATIONS

This Application is a 35 U.S.C. § 371 national phase application of PCT/EP02/10062, with an international filing date of Sep. 6, 2002, which claims priority to application EP 01203416.1, filed on Sep. 10, 2001, all of which are incorporated herein by reference in their entirety.

The present invention relates to a method for the preparation of hexahydro-furo[2,3-b]furan-3-ol as well as novel intermediates for use in said method. More in particular the invention relates to a stereoselective method for the preparation of hexahydro-furo[2,3-b]furan-3-ol, and to a method amenable to industrial scaling up.

Hexahydro-furo[2,3-b]furan-3-ol is an important pharmacological moiety present in the structure of retroviral protease inhibitors such as those described in Ghosh et al. in *J. Med. Chem.* 1996, 39(17), 3278–3290, EP 0 715 618, WO 99/67417, and WO 99/65870. Said publications are hereby incorporated by reference.

Several methods for the preparation of hexahydro-furo[2, 3-b]furan-3-ol (formula (7))

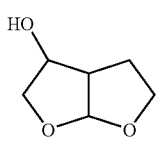

are known. Ghosh et al. in *J. Med. Chem.* 1996, 39(17), 3278–3290, describe an enantioselective synthesis to obtain both (3R,3aS,6aR) and (3S,3aR,6aS) hexahydro-furo[2,3-b] furan-3-ol in optically pure form starting from 3(R)-diethyl malate and 3(S)-diethyl malate respectively. This process comprises several steps such as an allylation step using lithium diisopropyl amide, followed by a reduction step, and further a Swern oxidation step followed by an ozonolytic cleavage and a hydroboration step using 9-borabicyclo [3.3.1]nonane (9-BBN). Ghosh et al. also disclose a racemic synthesis of both the (3R,3aS,6aR) and (3S,3aR,6aS) enantiomers of hexahydrofuro[2,3-]furan-3-ol followed by an enzymatic resolution of the final product. This latter synthesis starts from 2,3-dihydrofuran and comprises the step of treating said intermediate with N-iodosuccinimide and allyl alcohol followed by a radical cyclisation in the presence of a catalyst i.e. cobaloxime. An ozonolytic cleavage followed by a reduction step furnished the racemic hexahydro-furo [2,3-b]furan-3-ol. Optically active compound (3R,3aS,6aR) hexahydro-furo[2,3-b]furan-3-ol is obtained after enzymatic resolution followed by silica gel chromatography. Pezeck et al. *Tetrahedron Lett.* 1986, 27, 3715–3718 also describes a route for the synthesis of hexahydro-furo[2,3-b]-furan-3-ol using ozonolysis. Hexahydro-furo[2,3-b]furan-3-ol is also described as an intermediate in the synthesis of optically active perhydrofuro[2,3-b]furan derivatives (Uchiyama et al., *Tetrahedron Lett.* 2001, 42, 4653–4656.). The key step in this procedure is the oxyselenenylation of 2,3-dihydrofuran. This procedure is suitable for use at the laboratory level, yet not amenable for scaling up. Although the two synthetic routes described by Ghosh et al. provide (3R,3aS,6aR) and (3S,3aR,6aS) hexahydro-furo[2,3-b]furan-3-ol in reasonable yields and high enantiomeric excess, they both are only feasible on a laboratory scale, but, for a number of reasons, are not amenable to industrial scaling up. For example, these known routes suffer from the disadvantage of utilizing expensive materials, heavy metals and rare compounds, such as the N-iodosuccinimide, the catalyst cobaloxime, lithium diisopropyl amide and 9-BBN. The necessary ozonolysis step has the disadvantage of producing highly reactive and shock-sensitive ozonides and peroxides making this step too dangerous to be applied on industrial scale. Furthermore ozonolysis as well as Swern oxidation are highly exothermic and, as a consequence, have to be performed at very low temperatures. The racemic route needs an enzymatic resolution in the final step of the synthesis followed by silica gel purification. Furthermore, the racemic route suffers from the disadvantage of a low overall mass balance, originating from the fact that the resolution step, leading to the final enantiomerically pure compound, occurs in the last step of the synthesis whereby only a maximum of 50% yield of desired enantiomer can be obtained. Both art-known routes also produce a lot of waste such as solvents and salts in washings operations. Thus, these known methods are not suitable for the production of optically pure stereoisomers of hexahydro-furo[2,3-b]furan-3-ol on an industrial scale.

The main object of the present invention is to provide an improved method for producing hexahydro-furo[2,3-b]furan-3-ol, when compared to the art-known methods and their drawbacks. It is another object to provide a method for the synthesis of hexahydro-furo[2,3-b]furan-3-ol, which is suitable for industrial scaling-up. A further object of the present invention is to provide with a stereoselective method comprising steps wherein the stereochemistry of intermediates or final compounds is controlled, which allows the synthesis of the stereoisomers of hexahydro-furo[2,3-b]furan-3-ol. Another further object is to provide with a method which allows the production of hexahydro-furo[2,3-b]furan-3-ol in a overall yield equal or higher than for the above-described methods and with an enantiomeric excess higher than 50%. Another object of the present invention is to provide with a process for manufacturing hexahydro-furo[2,3-b]furan-3-ol which is produced from readily available starting materials and reagents. Another object of the present invention is to provide with novel intermediate compounds, which are useful as precursors in the synthesis of hexahydro-furo[2, 3-]furan-3-ol.

The authors of the present invention have surprisingly found a novel and inventive method for the synthesis of stereoisomeric mixtures or stereoisomerically pure forms of hexahydro-furo[2,3-b]furan-3-ol.

Thus, the present method involves the synthesis of hexahydro-furo[2,3-b]furan-3-ol starting from an intermediate of formula (1) wherein $P^1$ and $P^2$ represent each independently a hydrogen, a hydroxy-protecting group or may together form a vicinal-diol protecting group, transforming said intermediate of formula (1) into a nitromethane

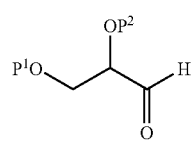

derivative of formula (3) wherein $R^1$ represents alkyl, aryl or aralkyl, $R^2$ represents hydrogen or $C(=O)OR^3$, $R^3$ represents an alkyl, aryl or aralkyl, or R³, if present, and R¹ taken together with the atoms to which they are attached may form a 6 to 8-membered cyclic group which may be optionally substituted with alkyl, aralkyl, or aryl,

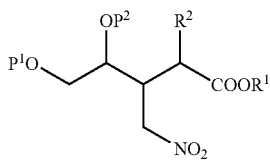

3 subsequently transforming said nitromethane derivative into a tetrahydrofuran derivative of formula (6) wherein OR⁴ represents an alcoholate such as an alkyloxy group, by for instance, making use of a Nef reaction,

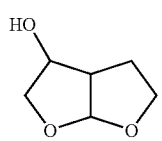

6 and then transforming the intermediate of formula (6) into hexahydro-furo[2,3-b]furan-3-ol of formula (7) by way of an intramolecular cyclisation reaction.

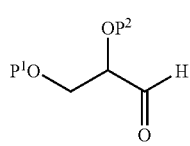

7

The above method has the further advantage of using readily available starting material, such as an O-protected glyceraldehyde. The reagents further used in said method are safe and available in bulk. Furthermore, each step of said method provides with the desired compound in good yield. Moreover, each step of said method can be performed stereoselective, which allows the synthesis of pure stereoisomeric forms of said compounds when using, where appropriate, optically pure starting material and reagents. Thus, the method according to the present invention is amenable to industrial scaling-up.

In a preferred embodiment, the present invention relates to a method for the synthesis of hexahydro-furo[2,3-b]furan-3-ol of formula (7), which comprises the steps of:
a) condensing an intermediate of formula (1)

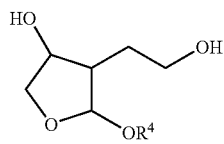

1 resulting in an α,β-unsaturated ester of formula (2), wherein P¹, P², R¹ and R² are defined as above,

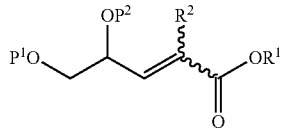

2 b) reacting said ester of formula (2) with nitromethane resulting in an intermediate of formula (3),

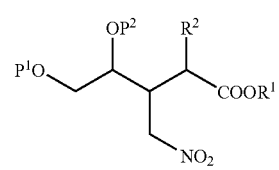

3 c) submitting said intermediate of formula (3) to a Nef reaction leading to intermediates of formula (4) and (4')

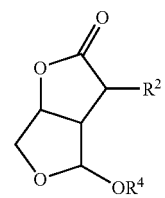

4

4' d) transforming said intermediates of formula (4) and (4') into an intermediate of formula (6) and,

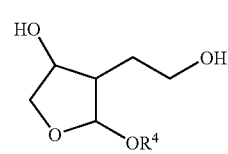

6 e) converting intermediate of formula (6) to the compound of formula (7) by an intramolecular cyclisation reaction.

In a more preferred embodiment, the present invention relates to a method for the synthesis of hexahydro-furo[2, 3-b]furan-3-ol of formula (7), which comprises the steps of:
a) condensing an intermediate of formula (1) with a suitable oxycarbonylmethylene reagent of formula CHR²R⁵—C (=O)—OR¹ wherein R¹ and R² are defined as above and R⁵ represents a hydrogen, a carboxylic ester, a phosphonium salt or a phosphonate ester,

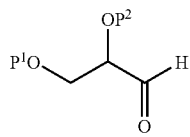

(1)

resulting in an α,β-unsaturated ester of formula (2), wherein $P^1$, $P^2$, $R^1$ and $R^2$ are defined as above,

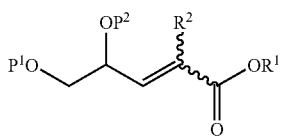

(2)

b) reacting said ester of formula (2) with nitromethane resulting in an intermediate of formula (3),

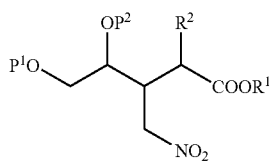

(3)

c) submitting said intermediate of formula (3) to a Nef reaction by treating it with a base and subsequently with a strong acid resulting in a mixture of intermediates of formula (4) and (4'), wherein $R^4$ is as defined above,

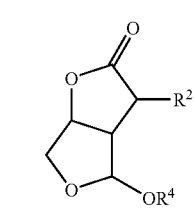

(4)

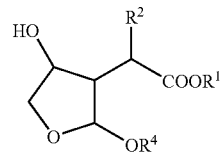

(4')

d) only in case $R^2$ is different from hydrogen, decarboxylating the intermediates of formula (4) and (4') thus forming intermediates of formula (5) and (5') respectively,

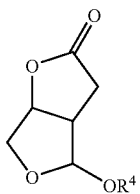

(5)

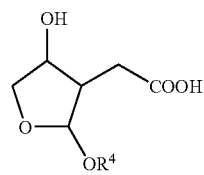

(5')

e) reducing intermediates of formula (4) and (4') wherein $R^2$ is hydrogen, or intermediates of formula (5) and (5') with a suitable reducing agent resulting in intermediate of formula (6) and,

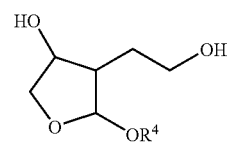

(6)

f) converting intermediate of formula (6) to the compound of formula (7) by an intramolecular cyclisation reaction.

The order of the above mentioned steps in said process may be different from the alphabetical order cited above. For example, step (a) and (b) of said process may be inverted provided that an oxycarbonylmethylene reagent of formula $CHR^2R^8$—(=O)—$OR^1$ is used instead of one of formula $CHR^2R^5$—C(=O)—$OR^1$ whereby $R^8$ differs from $R^5$ in that $R^8$ can not form a Wittig or Horner-Emmons reagent such as a phosphonium salt or a phosphonate ester. Also, in case $R^2$ is hydrogen, a reduction of the C(=O)—$OR^1$ moiety analogous to the one described in step e) may be performed prior to the Nef reaction of step (c).

Oxycarbonylmethylene reagents of formula $CHR^2R^5$—C(=O)—$OR^1$ wherein $R^5$ represents a carboxylic ester are for instance dicarboxylic esters of formula $R^1O$—C(=O)—$CHR^2$—C(=O)—$OR^1$. Oxycarbonylmethylene reagents of formula $CHR^2R^5$—C(=O)—$OR^1$ wherein $R^5$ represents a phosphonium salt may for instance have the formula $(R^6)_3P$=$CR^2$—C(=O)—$OR^1$ wherein $R^6$ is alkyl, aryl or aralkyl. Oxycarbonylmethylene reagents of formula $CHR^2R^5$—C(=O)—$OR^1$ wherein $R^5$ represents $(R^7O)_2P(=O)$— may for instance have the formula $(R^7O)_2P(=O)$—$CHR^2$—C(=O)—$OR^1$ wherein $R^7$ is alkyl, aryl or aralkyl.

Suitably, the invention relates to a method wherein $P^1$ and $P^2$ together form a vicinal-diol protecting group, and particularly, the vicinal-diol protecting group is an acid labile protecting group that remains unaffected during the base treatment step of the Nef reaction. Preferably, said vicinal-diol protecting group is selected from the group consisting of methylene, diphenylmethylene, ethylidene, 1-t-butylethylidene, 1-phenylethylidene, (4-methoxyphenyl)ethylidene, 2,2,2-trichloroethylidene, isopropylidene, cyclopentylidene, cyclohexylidene, cycloheptylidene, benzylidene, p-methoxybenzylidene, 2,4-dimethoxybenzylidene, 3,4-dimethoxybenzylidene and 2-nitrobenzylidene. In a most preferred embodiment, $P^1$ and $P^2$ together form a dialkyl methylene such as a isopropylidene or a 3-pentylidene radical.

Interesting vicinal-diol protecting groups are those protecting groups that do not cause an additional stereogenic center in the intermediates of formula (1), (2) and (3).

Suitably, $R^1$ and $R^3$ each independently are $C_{1-6}$alkyl, aryl or aryl$C_{1-6}$alkyl, in particular, $C_{1-6}$alkyl, more in particular, $R^1$ and $R^3$ each independently are methyl, ethyl, propyl, isopropyl, n-butyl, isobutyl, sec-butyl, tert-butyl and pentyl, and preferably, $R^1$ and $R^3$ each independently are methyl, ethyl or tert-butyl.

$R^1$ and $R^3$ when taken together, denoted as —$R^1$—$R^3$—, preferably are —$CH_2$— or —$CH_2$—$CH_2$— optionally substituted with $C_{1-6}$alkyl, aryl or aryl$C_{1-6}$alkyl.

Suitably, $R^4$ is a $C_{1-6}$alkyl, in particular, $R^4$ is methyl, ethyl, propyl, isopropyl, n-butyl, isobutyl, sec-butyl, tert-butyl and pentyl, and preferably, $R^4$ is methyl or ethyl.

In a preferred embodiment, the present invention relates to a stereoselective process for the preparation of pure stereoisomers of hexahydro-furo[2,3-b]furan-3-ol, in particular, (3R,3aS,6aR) hexahydro-furo[2,3-b]furan-3-ol.

The term "hydroxy-protecting group" as used herein refers to a substituent which protects hydroxyl groups against undesirable reactions during synthetic procedures such as those O-protecting groups disclosed in Greene, "Protective Groups In Organic Synthesis," (John Wiley & Sons, New York (1981)). O-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The term "vicinal-diol protecting group" as used herein refers to protecting groups in the acetal or ketal form and in the orthoester form. Specific examples of the protecting group in the acetal or ketal radical form include methylene, diphenylmethylene, ethylidene, 1-t-butylethylidene, 1-phenylethylidene, (4-methoxyphenyl)ethylidene, 2,2,2-trichloroethylidene, isopropylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, etc. and specific examples of the protecting group in the orthoester form include methoxymethylene, ethoxymethylene, dimethoxymethylene, 1-methoxyethylidene, 1-ethoxyethylidene, 1,2-dimethoxy-ethylidene, alpha-methoxybenzylidene, 1-(N,N-dimethylamino) ethylidene, alpha-(N,N-dimethylamino) benzylidene, 2-oxacyclopentylidene, etc.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms ($C_{1-20}$alkyl), suitably 1 to 10 carbon atoms ($C_{1-10}$alkyl), preferably 1 to 8 carbon atoms ($C_{1-8}$alkyl), more preferably 1 to 6 carbon atoms ($C_{1-6}$alkyl), and even more preferably 1 to 4 carbon atoms ($C_{1-4}$alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl and the like. The term "aryl" as used herein, includes an organic radical derived from an aromatic hydrocarbon by removal of one hydrogen, and include monocyclic and polycyclic radicals, such as phenyl, biphenyl, naphthyl. The term "aralkyl" as used herein, relates to a group of the formula aryl-alkyl in which alkyl and aryl are as defined above. Examples of aralkyl radicals include benzyl, phenethyl and the like.

The term "alkoxy" as used herein alone or as part of a group refers to an alkyl ether radical wherein the term alkyl is as defined above. Examples of alkyl ether radical include methoxy, ethoxy, n-propoxy, isopropoxy, n-butoxy, iso-butoxy, sec-butoxy, tert-butoxy and the like.

The term "stereoselective process" and "stereoselective step" as used herein, essentially relates to a process or a step wherein when using an optically pure starting material, pure stereoisomeric forms of the compounds of interest are obtained at the end of said process or said step.

The term "stereochemically isomeric forms" or "stereoisomeric forms", as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, enantiomers and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

Pure stereoisomeric forms of the intermediates of formula (1) and of the starting material or reagents as mentioned herein are defined as isomers substantially free of other enantiomeric or diastereomeric forms of the same basic molecular structure of said compounds, starting material or reagents. Suitably, the term "stereoisomerically pure" compounds, starting material or reagents relates to compounds, starting material or reagents having a stereoisomeric excess of at least 50% (i.e. minimum 75% of one isomer and maximum 25% of the other possible isomers) up to a stereoisomeric excess of 100% (i.e. 100% of one isomer and none of the other), preferably, compounds, starting material or reagents having a stereoisomeric excess of 75% up to 100%, more preferably, compounds, starting material or reagents having a stereoisomeric excess of 90% up to 100%, even more preferred compounds or intermediates having a stereoisomeric excess of 94% up to 100% and most preferred, having a stereoisomeric excess of 97% up to 100%. The terms "enantiomerically pure" and "diastereomerically pure" should be understood in a similar way, but then having regard to the enantiomeric excess, respectively the diastereomeric excess of the mixture in question.

Although the methods for preparing stereoisomerically pure compounds of formula (7) according to the present invention will advantageously employ stereoisomerically pure starting materials, it may be desirable to further purify the compounds and intermediates by the application of art-known purification procedures. For instance, enantiomers may be separated from each other by the selective crystallization of their diastereomeric salts with optically active acids. Alternatively, enantiomers may be separated by chromatographic techniques using chiral stationary phases.

Despite the fact that hexahydro-furo[2,3-b]furan-3-ol has three stereogenic centers and theoretically 8 different stereoisomers should occur, only 4 stereoisomers are deemed to exist. This is due to the rigidity of the bicyclic ringstructure in hexahydro-furo-[2,3-b]furan-3-ol which causes the trans-fused stereoisomers thereof to be thermodynamically unfavorable. Only stereoisomers having a cis-fused configuration are thermodynamically stable, thus reducing the number of stereoisomers of hexahydro-furo[2,3-b]furan-3-ol to the following:

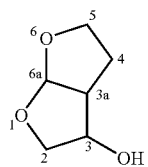

| Compound | configuration atom 3 | configuration atom 3a | configuration atom 6a | Stereochemical descriptor |
|---|---|---|---|---|
| 7.1 | R | S | R | (3R,3aS,6aR) |
| 7.2 | R | R | S | (3R,3aR,6aS) |
| 7.3 | S | R | S | (3S,3aR,6aS) |
| 7.4 | S | S | R | (3S,3aS,6aR) |

The method of the present invention may be further understood by reference to Scheme 1, wherein $P^1$ and $P^2$ represent each independently a hydrogen, a hydroxy-protecting group or may together form a vicinal-diol protecting group, $R^1$ represents a alkyl, aryl or aralkyl, $R^2$ represents a hydrogen or $COOR^3$, $R^3$ represents a alkyl, aryl or aralkyl, or $R^3$, if present, and $R^1$ taken together with the atoms to which they are attached may form a 6 to 8-membered cyclic group which may be optionally substituted with an alkyl, aryl or aralkyl; and $R^4$ represents alkyl.

Scheme 1 depicts a synthetic method for the synthesis of hexahydro-furo[2,3-b]furan-3-ol (7) starting with intermediate of formula (1) wherein, $P^1$ and $P^2$ represent each independently a hydrogen, a hydroxy-protecting group or may together form a vicinal-diol protecting group.

The above-mentioned hydroxy-protecting group and vicinal-diol protecting group can be readily cleaved by methods know in the art such as hydrolysis, reduction, etc., and are appropriately selected depending on the protecting group used. According to a more preferred embodiment, the vicinal-diol protecting group is an acid labile protecting group, wherein the term "acid labile" as used herein refers to vicinal-diol protecting groups that are readily cleaved using acidic conditions.

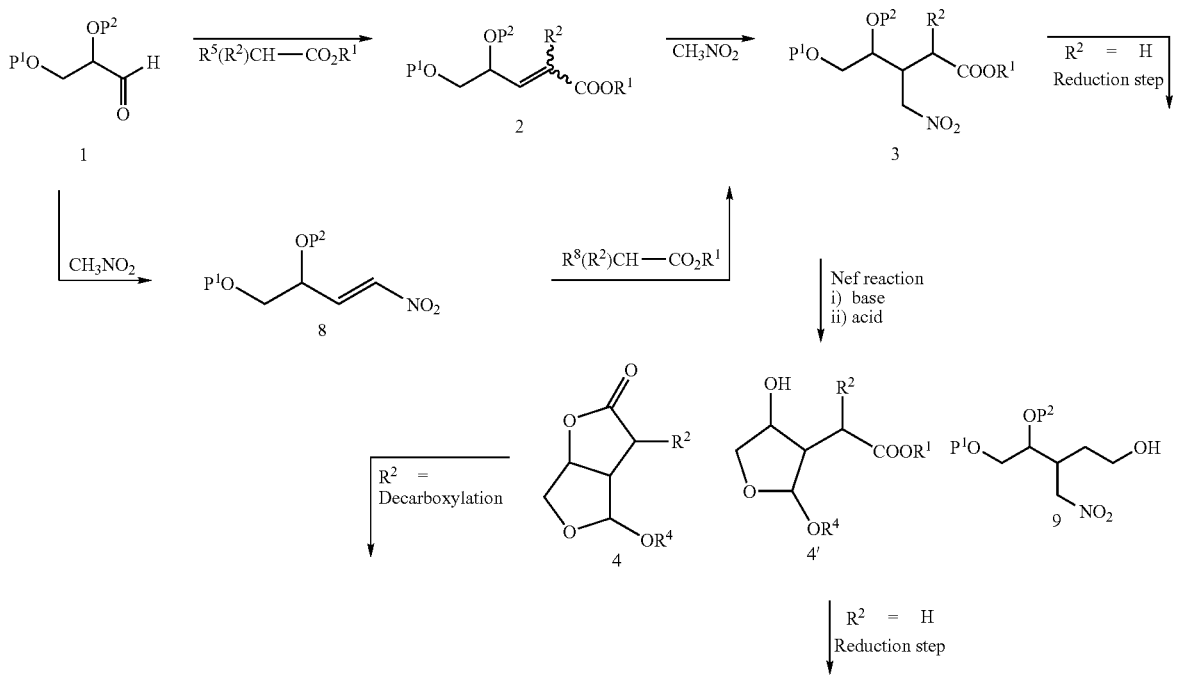

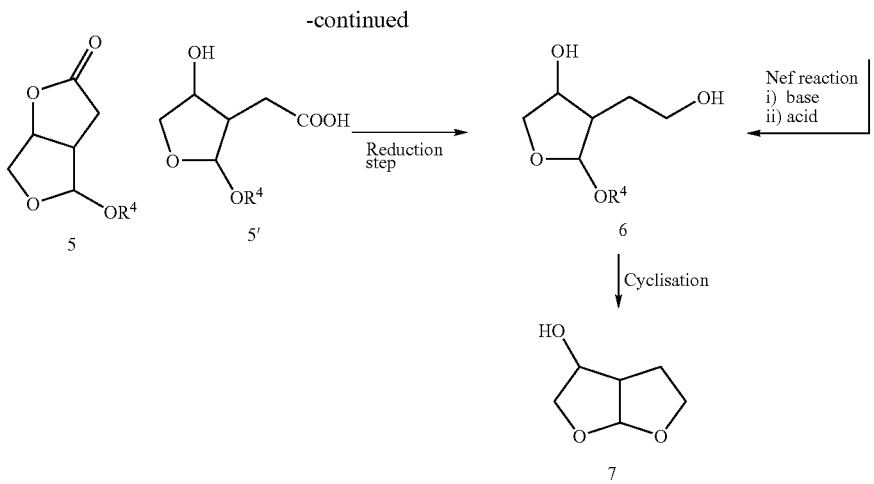

Several of the protected glyceraldehydes of formula (1) used in the present invention are known compounds. Enantioselective as well as racemic versions of the synthesis of these protected glyceraldehyde derivatives have been described in the literature. For example, the preparation of 2,3-O-isopropylidene-S-glyceraldehyde is described in C. Hubschwerlen, *Synthesis* 1986, 962, the preparation of 2,3-O-isopropylidene-R-Glyceraldehyde is described in C. R. Schmid et al., *J. Org. Chem.* 1991, 56, 4056–4058, and the preparation of 2,3-O-isopropylidene-(R,S)-glyceraldehyde is described in A. Krief et al., *Tetrahedron Lett.* 1998, 39, 1437–1440. Said intermediate of formula (1) may be commercially available, or prepared prior to the reaction or formed in situ. According to a preferred embodiment, said compound is formed in situ.

In the first step of a preferred method for the preparation of a compound of formula (7), an α,β-unsaturated ester of formula (2) is prepared from intermediate of formula (1) by a condensation reaction with an appropriate oxycarbonylmethylene reagent in the presence of a suitable solvent at a suitable temperature.

In general, any reaction procedure introducing a =C($R^2$)C(=O)$OR^1$ moiety in the starting material of formula (1) can be utilized. For instance, such conversion of intermediate of formula (1) to intermediate of formula (2) can be performed using a reaction procedure that makes use of an oxycarbonylmethylene moiety of formula $CHR^2R^5$—C(=O)$OR^1$ such as, for example, via a Wittig reaction using phosphorus ylides of the formula $(R^6)_3P=CR^2$—C(=O)$OR^1$; via a Horner-Emmons reaction using phosphonates of the formula $(R^{7O})_2P(=O)$—$CHR^2$—C(=O)$OR^1$, in the presence of a base; or via a Knoevenagel type of condensation reaction using malonate derivatives of the formula $R^1OC(=O)$—$CHR^2$—C(=O)$OR^1$, in the presence of a base, wherein $R^1$, $R^2$, $R^6$ and $R^7$ have the same meaning as that defined above. Another alternative may be to use a Reformatsky reagent such as oxycarbonylmethylenezinc halides. Yet another alternative involves the use of precursors of —C(=O)—O— moieties such as a cyanide. These types of reaction procedures are described in detail in Jerry March's handbook of Advanced Organic Chemistry.

According to a preferred embodiment, said oxycarbonylmethylene reagent is selected from the group consisting of (alkoxycarbonylmethylene)phosphoranes such as, for example, (carbethoxymethylene)triphenylphosphorane, (methoxycarbonylmethylene)triphenylphosphorane, (carbethoxymethylene)trimethylphosphorane, (carbethoxymethylene)triethylphosphorane, (carbethoxymethylene)tricyclohexylphosphorane or (carbethoxymethylene)tributylphosphorane; alkyl dialkylphosphonoacetates and alkyl diarylphosphonoacetates such as, for example, triethylphosphonoacetate, ethyl dimethylphosphonoacetate, methyl diethylphosphonoacetate or ethyl diphenylphosphonoacetate; alkyl malonate esters such as, for example, dimethylmalonate, diethyl malonate, di-tert-butyl malonate and malonic acid cyclic isopropylidene ester.

Examples of suitable bases include, but are not limited to, alkylamines and aromatic amines such as: pyridine, pyrrolidine, piperidine, morpholine, N-methylmorpholine, 1,4-diazabicyclo[2.2.2]octane (DABCO), 1,3-diazabicyclo[3.4.0]non-5-ene (DBN), 1,8-diazabicyclo[5.4.0]undec-7-ene (DBU), N,N-diethylaniline, N,N-dimethylaminopyridine(s), quinoline, triethylamine and N,N-diisopropylethylamine; as well as sodium-, potassium- or lithium hydride; sodium-, potassium-, lithium- or cesium carbonate; sodium-, potassium-, lithium- or cesium carbonate and alkoxide bases such as sodium, lithium or potassium methoxides, ethoxides, butoxides, t-butoxides, and t-amyloxides; butyllithium and lithium diisopropylamide.

Suitable solvents for this reaction are any hydrocarbon, ether, halogenated hydrocarbon, or aromatic solvents known in the art for the condensation reaction. These would include, but are not limited to, pentane, hexane, heptane, toluene, xylene(s), benzene, mesitylene(s), t-butylmethyl ether, dialkyl ethers (ethyl, butyl), diphenyl ether, chlorobenzene, methylene chloride, chloroform, carbon tetrachloride, acetonitrile, dichlorobenzene, dichloroethane, trichloroethane, cyclohexane, ethylacetate, isopropyl acetate, tetrahydrofuran, dioxane, methanol, ethanol, and isopropanol.

In case a Knoevenagel type of condensation is employed, it may also be convenient to use an acid anhydride, such as acetic anhydride, as a dehydrating agent in the condensation reaction. The fact that water is removed from the reaction medium will push the equilibrium of the reaction towards the α,β-unsaturated diester resulting in the completion of the reaction. Acetic anhydride may be replaced by tetrahydrofurane, n-methyl-morpholine, or isoprpylacetate. The addition of a base may increase the yield of the Knoevenagel reaction. Examples include the use of alkylamines such as triethylamine. Preferably, such base is added in small amounts. Alternatively, a Knoevenagel reaction may be performed using TiCl$_4$.

Suitable temperature for the condensation reaction ranges between room temperature and refluxing temperature of the suitable solvent, a condition readily determined by one skilled in the art of organic synthesis. It is preferred to run the reaction at room temperature.

Depending on the type of condensation reaction and on the reagent used, α,β-unsaturated mono-esters of formula (2) (when $R^2$=H) or α,β-unsaturated di-esters of formula (2) (when $R^2$=COOR$^3$) can be synthesized. α,β-Unsaturated mono-esters of formula (2) ($R^2$=H) and di-esters whereby $R^3$ and $R^1$ are different, can be obtained with E or Z stereochemistry around the double bond. The E/Z isomer ratio depends from the applied condensation reagent and the reaction conditions, the reaction solvent in particular.

The next step of such preferred method consists of the addition of nitromethane as a formyl group precursor, to the α,β-unsaturated ester intermediate of formula (2), in the presence of a suitable base, resulting in a 1,4-addition product of formula (3). This nitromethane addition step occurs diastereoselectively. The newly formed stereocenter at carbon atom number 3 (C-3) of the pentanoate skeleton is controlled by the stereochemistry at the oxygenated position at carbon atom number 4 (C-4).

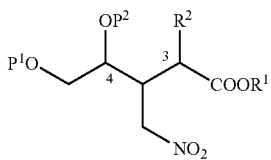

The syn/anti ratio is further controlled by the type of α,β-unsaturated ester (2) (E or Z, mono- or di-ester), the type of base used and the reaction conditions such as reaction solvent and reaction temperature. The syn addition product usually predominates.

Examples of suitable bases include but are not limited to DBN (1,3-Diazabicyclo [3.4.0]non-5-ene) and DBU (1,8-Diazabicyclo [5.4.0]undec-7-ene), triethylamine, pyrrolidine, piperidine, morpholine, N-methylmorpholine, 1,4-diazabicyclo[2.2.2]-octane (DABCO), dimethylaminopyridine (DMAP), sodium hydroxide, potassium hydroxide, lithium hydroxide, calciumdihydroxide, bariumdihydroxide, sodium carbonate, potassium carbonate, sodium hydride, potassium hydride, sodium methoxide, lithium methoxide, sodium ethoxide, potassium ethoxide, lithium tert-butoxide, sodium tert-butoxide, potassium tert-butoxide, tetrabutylammonium fluoride, tetrabutylammonium hydroxide. Examples of suitable solvents include, but are not limited to pentane, hexane, heptane, toluene, xylene(s), benzene, mesitylene(s), t-butyl-methyl ether, dialkyl ethers (ethyl, butyl), diphenyl ether, chlorobenzene, methylene chloride, chloroform, carbon tetrachloride, acetonitrile, dichlorobenzene, 1,2-dichloroethane, and 1,1,1-trichloroethane, cyclohexane, tetrahydrofuran, dioxane, methanol, ethanol, isopropanol, dimethyl sulfoxide (DMSO), dimethyl formamide (DMF), N-methylpyrrolidone (NMP). The reaction temperature is set in the range of about 0 to about 100° C., preferably in the range of about 10 to about 50° C., more preferably at about room temperature.

Intermediate of formula (3) may be alternatively prepared by a process comprising the steps of first condensing intermediate of formula (1) with nitromethane, resulting in an intermediate of formula (8) and secondly, reacting said intermediate of formula (8) with a suitable oxycarbonylmethylene reagent of formula CHR$^2$R$^8$—C(=O)—OR$^1$ resulting in said intermediate of formula (3).

It is to be understood that a person skilled in the art may employ other art-known reaction procedures to arrive at intermediate of formula (3) starting from an intermediate of formula (1).

The next step in the methods according to the present invention is to form an intermediate of formula (6) starting from an intermediate of formula (3).

One way of achieving this involves the transformation of an intermediate of formula (3) to the corresponding formyl derivative via a Nef reaction. This step is performed by treating intermediate of formula (3) with first a base and then with a strong acid resulting in intermediates of formula (4) and (4').

The Nef reaction is usually defined as the conversion of a primary or a secondary nitroalkane into the corresponding carbonyl compound (N. Kornblum Organic reactions 1962, 12, 101 and H. W. Pinnick Organic Reactions 1990, 38, 655). In the classical procedure, the nitroalkane is deprotonated with a base in α-position of the nitro function, followed by acid-catalyzed hydrolysis of the intermediate 'nitronate' salt via addition to a strong acid present in excess, to give the carbonyl derivative.

Suitable bases may be selected by one of skill in the art of organic synthesis. Suitable bases include, but are not limited to, inorganic bases such as alkali metal, alkali earth metal, and ammonium hydroxides and alkoxides. Suitable bases also include, but are not limited to, metal amides and alkyl lithiums. Examples of suitable strong bases are lithium diisopropyl amide, sodium amide, sodium methoxide, potassium t-butoxide, sodium butoxide, calcium dihydroxide, barium dihydroxide, methyllithium, butyllithium, hexyllithium, phenyllithium, and quaternairy alkylammonium hydroxides, DBN (1,3-Diazabicyclo [3.4.0]non-5-ene) and DBU (1,8-Diazabicyclo [5.4.0]undec-7-ene), 1,4-diazabicyclo[2.2.2]octane (DABCO), potassium carbonate, sodium carbonate.

The term "strong acid" as used herein, refers to any conventional strong acid such as the strong, inorganic acids, e.g., hydrochloric acid and sulfuric acid, and the strong organic acids, e.g., benzenesulfonic acid and trichloroacetic acid. The preferred strong acids are concentrated sulfuric acid or hydrochloric acid.

The use of a strong acid causes the deprotection of the acid labile protecting groups, thus forming a diol intermediate of which the primary alcohol condenses with the formyl group to a cyclic hemi-acetal of formula

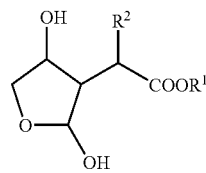

Using anhydrous conditions and an alcohol solvent such as methanol or ethanol (generically denoted as R$^4$—OH) the cyclic methyl acetal or ethyl acetal of the formyl group is obtained instead. Besides this classical base/acid procedure, Nef-conversions can be accomplished using a broad variety of oxidizing as well as reducing agents known in the art.

According to a preferred embodiment, suitable alcohol solvents are selected from the group consisting of methanol, ethanol and isopropanol.

Said Nef reaction can be carried out at temperatures that range between about −78° C. and about 55° C., the preferred temperatures lying between about −18° C. and about room temperature. The reaction times can range up to about 24 hours and suitably range between about 1 hour and about 24 hours.

According to a preferred embodiment, intermediate of formula (3) is treated with a base and subsequently added to a concentrated strong acid alcoholic solution leading to the conversion of the nitromethane radical of intermediate of formula (3) to a formyl group. Concurrently, the acid treatment also catalyses the cleavage of the protecting groups $P^1$ and $P^2$, resulting in an intramolecular acetal formation leading to intermediates of formula (4) and (4'). The $R^4$ substituent in the intermediates of formula (4) and (4') originate from the alcohol $R^4$—OH.

The bicyclic intermediate of formula (4) is the expected reaction product from the intermediate of formula (3) in a syn configuration while intermediate of formula (4') is the expected reaction product from the intermediate of formula (3) in an anti configuration. The trans-configuration of the substituents at carbon atom number 3 (C-3) and carbon atom number 4 (C-4) on the tetrahydrofuran ring of intermediate of formula (4') prevents the second lactone ring formation as in intermediate of formula (4).

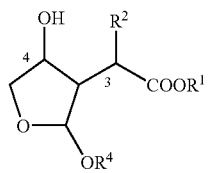

At this stage of the synthesis procedure, when $R^2$ is $COOR^3$, a decarboxylation step is implemented. Said decarboxylation step consists of the removal of —C(=O)—$OR^3$ in intermediates of formula (4) and (4'). In a preferred embodiment, the decarboxylation step is performed by treating intermediates of formula (4) and (4') with a suitable base, such as sodium hydroxide or potassium hydroxide, under heating conditions, resulting, after acidification, in the intermediates of formula (5) and (5') respectively. Concurrently, $R^1$ in intermediate of formula (4') is replaced by hydrogen as can be noted in the formula in intermediate (5').

The bicyclic lactone derivative of formula (5) is the expected reaction product from intermediate of formula (4), while the carboxylic acid derivative of formula (5') is the expected reaction product from intermediate of formula (4'). The trans-configuration of the substituents at C-3 and C-4 on the tetrahydrofuran ring of intermediate formula (5') prevents the second lactone ring formation as in intermediate of formula (5).

At this stage of the synthesis procedure, the intermediates (4) and (4') or the intermediates (5) and (5') can be separated from one another using art-known chromatographic techniques. In addition to chromatographic techniques, the intermediate of formula (5') can be separated from lactone of formula (5) by means of acid/base extraction. Typically, intermediates of formula (5') can be extracted with a basic aqueous solution such as a sodium bicarbonate solution from a mixture of intermediates of formula (5) and (5') in an organic non-water mixable solvent. Suitable organic non-water miscible solvents are any hydrocarbon, ether, halogenated hydrocarbon, or aromatic solvents. These would include, but are not limited to, pentane, hexane, heptane, toluene, xylene(s), benzene, mesitylene(s), t-butylmethyl ether, dialkyl ethers (ethyl, butyl), diphenyl ether, chlorobenzene, dichloromethane, chloroform, carbon tetrachloride, acetonitrile, dichlorobenzene, 1,2-dichloroethane, 1,1,1-trichloroethane, ethyl acetate and isopropyl acetate.

In order to improve the extraction yield of lipophilic compounds, water soluble salts may be added to the mixture prior to extraction. A preferable salt includes NaCl. The addition of water miscible salts may increase the yield of the extraction.

Alternatively, a mixture of intermediates (4) and (4'), or intermediates (5) and (5') can be used without further separation, particularly when they were stereoselectively synthesized.

In the following step, intermediates of formula (4) and/or (4') wherein $R^2$ is hydrogen, or the intermediates of formula (5) and/or (5') are reduced with a suitable reducing agent, resulting in intermediate of formula (6).

The reduction step can conveniently be accomplished by treatment of intermediates of formula (4) and/or (4') wherein $R^2$ is hydrogen, or (5) and/or (5') with metal hydrides such as borane complexes, diborane, lithium borohydride, sodium borohydride-LiCl, diisobutylaluminum hydride or lithium aluminum hydride in suitable anhydrous solvents. Examples of suitable anhydrous solvent include but are not limited to dichloromethane, toluene, xylene, benzene, pentane, hexane, heptane, petrol ether, 1,4-thioxane, diethyl ether, diisopropyl ether, tetrahydrofuran, 1,4-dioxane, 1,2-dimethoxiethane, and in general any anhydrous solvent susceptible to being used in a chemical reduction process using the reagents cited above. Said reduction step can be carried out at temperatures that ranges between about −78° C. and about 55° C., the preferred temperatures lying between about −18° C. and about room temperature. The reaction time may range up to about 24 hours, and suitably vary between about 2 and about 24 hours. According to a preferred embodiment, the reduction step is performed using lithium borohydride in tetrahydrofuran. Alternatively, reduction may be accomplished using catalytic hydrogenation. Catalytic hydrogenation may suitably be performed using $H_2$ in combination with metals, including Pd. Pt, Ni and carbon.

In case $R^2$ is a hydrogen, an alternative route may be followed in preparing an intermediate of formula (6) from an intermediate of formula (3). In any of these two alternatives, a Nef procedure is employed. Thus, the conversion of intermediate of formula (3) to intermediate of formula (6), may be alternatively performed by a process comprising the steps of first reducing intermediate of formula (3) with a suitable reducing agent, resulting in an intermediate of formula (9) and secondly submitting the obtained intermediate of formula (9) to a Nef reaction by treatment with a base and then with a strong acid resulting in an intermediate of formula (6).

The last step consists of converting an intermediate of formula (6) to the desired compound of formula (7) by a cyclisation reaction. The cyclisation reaction occurs via an intramolecular transacetalisation reaction and can be performed in any acid-compatible organic solvent or a combination of a water miscible solvent and water and in the presence of a strong organic or inorganic acid. Said reaction is suitably performed by treatment of intermediate of formula (6) with a catalytic amount of a strong acid. In a preferred embodiment, the strong acid is selected from group consisting of hydrochloric acid and sulfuric acid. Said cyclisation step can be carried out at temperatures that range between about −78° C. and about 55° C., the preferred temperatures lying between about −18° C. and about room temperature.

Pure stereoisomeric forms of the above-mentioned compounds and intermediates may be synthesized by said above-described synthesis procedures. For instance, enantiomerically pure starting materials will be employed.

According to a preferred embodiment said above-described method is suitable for the preparation of (3R,3aS, 6aR) hexahydro-furo[2,3-b]furan-3-ol of formula (7.1)

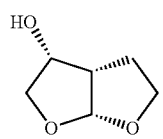

7.1

In a first step, an intermediate of formula (1a) is reacted with a suitable oxycarbonylmethylene reagent as described above resulting in an α,β-unsaturated ester of formula (2a) wherein $P^1$, $P^2$, $R^1$ and $R^2$ have the same meaning as that defined above. The reaction conditions are the same as those described previously for the condensation step. Intermediate (1a) may be preheated prior to a Knoevenagel reaction. Suitable preheating temperatures range from 40–70° C., preferably 50–65° C. The intermediate may then be cooled before the reaction. The order of adding the reagents may influence the yield of the reaction. For instance, in case a Knoevenagel type of condensation is used, it may be convenient to add the oxycarbonylmethylene reagent to intermediate (1a) prior to adding the dehydrating reagent. The manner of adding the dehydrating reagent may influence the yield of the reaction. The dehydrating reagent may be added slowly i.e. by dosing. After adding the dehydrating reagent, the reaction may be performed at temperatures in the range 20–60° C., preferably in the range 35–55° C.

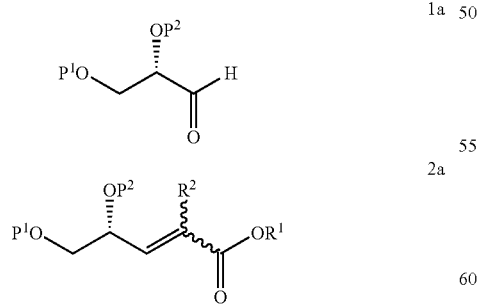

1a

2a

In a second step, said ester of formula (2a) is reacted with nitromethane in the presence of a suitable base, resulting in intermediates of formula (3a) and (3b), wherein $R^1$, $R^2$, $P^1$ and $P^2$ are defined as above.

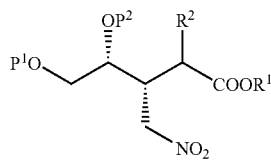

3a

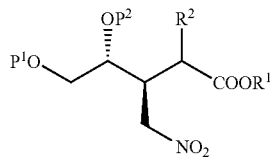

3b

The reaction conditions are the same as those previously described for the nitromethane addition step. The reaction is preferably carried out in an alcoholic solvent in the presence of a non-nucleophilic base such as DBU or sodium methoxide, at room temperature. Depending on the starting material and reaction conditions, this step can be performed stereoselectively.

The next step consists in the transformation of intermediates of formula (3a) and (3b) to the corresponding formyl derivatives via a Nef reaction. According to a preferred embodiment intermediates of formula (3a) and (3b) are treated with a base and subsequently added to a concentrated strong acid alcoholic solution leading to the conversion of the nitromethane radical of intermediates of formula (3a) and (3b) to a formyl group. Concurrently, the acid treatment also catalyses the cleavage of the protecting groups $P^1$ and $P^2$, resulting in an intramolecular acetal formation leading to intermediates of formula (4a) and (4'a), respectively, wherein $R^1$, $R^2$ and $R^4$ are defined as above. Examples of a strong acid alcoholic solution include sulfuric acid in $CH_3OH$. The temperature during treatment with a strong acid alcoholic solution is room temperature or lower. Preferably, the temperature is below 15° C., more preferably, the reaction is performed below 10° C.

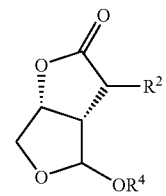

4a

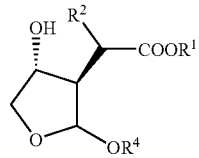

4'a

The reaction conditions are the same as those previously described for the Nef reaction.

At this stage of the synthesis procedure, when $R^2$ is $COOR^3$, a decarboxylation step is implemented for intermediates of formula (4a) and (4'a). The decarboxylation step consists of the removal of the —C(=O)—OR³ in intermediates of formula (4a) and (4'a). In a preferred embodiment the decarboxylation step is performed by treating intermediates of formula (4a) and (4'a) with a suitable base, such as sodium hydroxide or potassium hydroxide, under heating conditions, resulting, after acidification, in the decarboxylated products of formula (5a) and (5'a) respectively. Concurrently, R¹ in intermediate of formula (4') is replaced by hydrogen, resulting in a carboxylic acid moiety in intermediate (5'a).

Decarboxylation can also be performed using halides. Suitable reagents include KI, NaCl, LiI, LiBr and KBr, preferably KI. KI can be dissolved in a solvent such as N-methylpyrrolidone.

Alternatively, decarboxylation can be performed in buffered aqueous solutions. A suitable buffer includes citric acid buffer at pH=6. The decarboxylation reaction is then performed at elevated temperatures, suitably between 50° C. and reflux temperature. Preferably, the reaction temperature is above 80° C.

The decarboxylated mixture can be neutralized using strong acidic resins including DOWEX-H+® or mild acidic resins including AMBERJET®. Said resins can also be used for the cyclization reaction. Mild acidic resins of type AMBERJET® are also suitable for neutralizing the reaction.

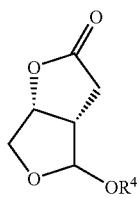

5a

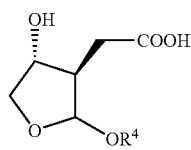

5'a

In the next step, intermediate of formula (4'a), when R² is a hydrogen atom, or the intermediate of formula (5'a) is separated from intermediate of formula (4a) or (5a) respectively, by means of chromatography or acid/base extraction. Intermediate of formula (4'a) or (5'a) can be extracted from the reaction mixture using art-known methods such as with a basic aqueous solution like sodium bicarbonate solution in an organic non-water miscible solvent. The reaction is further carried out with isolated intermediate of formula (4a) or (5a).

Intermediate (5a) can be crystallized using organic solvents. Suitable solvents include isopropylalcohol, ethylacetate, ethanol and methylisobutylketon. An interesting solvent is isopropylalcohol.

In the next step, intermediate of formula (4a) or (5a) is reduced with a suitable reducing agent resulting in intermediate of formula (6a), wherein R⁴ is defined as above.

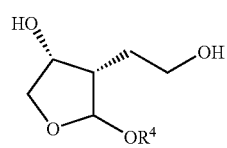

6a

The reduction step can be accomplished using the same conditions as previously described for the reduction step. According to a preferred embodiment, this step is performed using lithium borohydride in tetrahydrofuran. Alternatively, the reduction can be performed using $LiAlH_4$ or $NaBH_4$ in the presence of LiCl. Catalytic hydrogenation can also be used. Catalytic hydrogenation can be performed using hydrogen gas in the presence of a suitable catalyst. Examples of catalysts suitable for catalytic hydrogenation including nickel, palladium and platina. Suitably, the catalyst is present on an inert surface such as charcoal.

The last step consists of converting intermediate of formula (6a) to the compound of formula (7.1) by a cyclisation reaction. The cyclisation reaction occurs via an intramolecular transacetalisation reaction. Said reaction is preferably performed by treatment of intermediate of formula (6a) with a catalytic amount of a strong acid. In a preferred embodiment, the strong acid is selected from group consisting of hydrochloric acid and sulfuric acid. In one embodiment, the cyclization is performed at low temperature. Preferably, the temperature is below 15° C., more preferably, below 5° C. Following acid treatment, the mixture is neutralized using a suitable base and compound 7.1 is isolated.

Said above-described method is suitable for the preparation of (3R,3aR,6aS) hexahydro-furo[2,3-b]furan-3-ol of formula (7.2), by following the sequence of reactions described above.

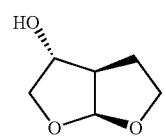

7.2

The reaction conditions of the condensation step, and the nitromethane addition step are controlled such that intermediate of formula (3b) is obtained in the highest possible yield, by changing for example the type of base used, the solvent and the reaction temperature. After the Nef reaction, the next step consists of isolating intermediates of formula (4'a) or (5'a) and then reducing said intermediate to obtain intermediate of formula (6b),

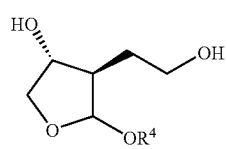

6b which is further cyclised to compound of formula (7.2).

Similarly, (3S,3aR,6aS) hexahydro-furo[2,3-b]furan-3-ol of formula (7.3), can be obtained by a method according to the present invention, starting from optically pure intermediate of formula (1b).

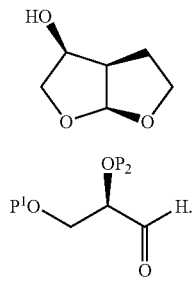

7.3

1b

In a first step an intermediate of formula (1b) is reacted with a suitable oxycarbonylmethylene reagent resulting in an α,β-unsaturated ester of formula (2b), wherein $P^1$, $P^2$, $R^1$ and $R^2$ have the same meaning as that defined above.

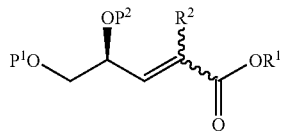

2b

The reaction conditions are the same as that previously described for the condensation step.

In a second step, said ester of formula (2b) is reacted with nitromethane in the presence of a suitable base, resulting in intermediates of formula (3c) and (3d), wherein $R^1$, $R^2$, $P^1$ and $P^2$ are defined as above.

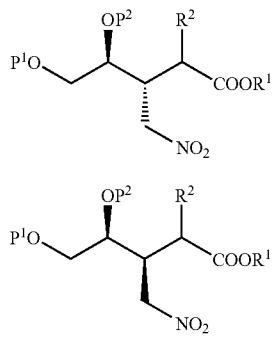

3c

3d

The reaction conditions are the same as that previously described for the nitromethane addition step. The reaction is preferably carried out in an alcoholic solvent in the presence of a non-nucleophilic base such as DBU, at room temperature.

The next step consists in the transformation of intermediates of formula (3c) and (3d) to the corresponding formyl derivatives via a Nef reaction. According to a preferred embodiment intermediates of formula (3c) and (3d) are treated with a base and subsequently added to a concentrated strong acid alcoholic solution. The acid treatment also catalyses the cleavage of the protecting groups $P^1$ and $P^2$, resulting in an intramolecular acetal formation leading to intermediates of formula (4b) and (4'b), respectively, wherein $R^1$, $R^2$ and $R^4$ are defined as above.

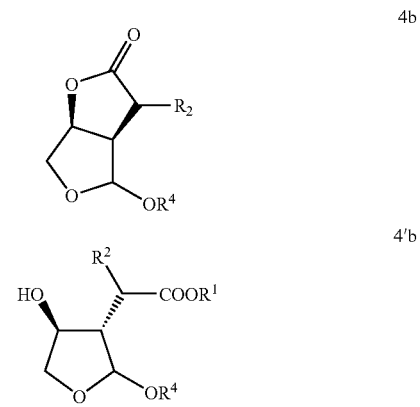

4b

4'b

The reaction conditions are the same as those previously described for the Nef reaction.

At this stage of the synthesis procedure, when $R^2$ is $COOR^3$, a decarboxylation step is implemented for intermediates of formula (4b) and (4'b). The decarboxylation step consists of the removal of the —C(=O)—$OR^1$ in intermediates of formula (4b) and (4'b). In a preferred embodiment the decarboxylation step is performed by treating intermediates of formula (4b) and (4'b) with a suitable base, such as sodium hydroxide or potassium hydroxide, under heating conditions, resulting, after acidification, in the decarboxylated products of formula (5b) and (5'b) respectively. Concurrently, $R^1$ in intermediate of formula (4'b) is replaced by hydrogen, resulting in a carboxylic acid moiety in intermediate (5'b).

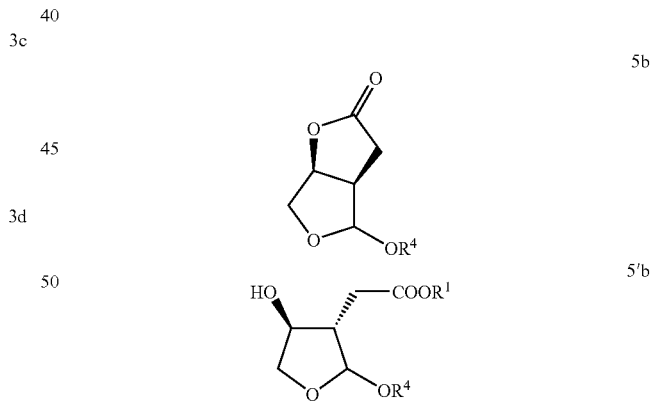

5b

5'b

In the next step, intermediate of formula (4'b) wherein $R^2$ is a hydrogen atom, or intermediate of formula (5'b), is separated from intermediate of formula (4b) or (5b) by means of chromatography or acid/base extraction. The reaction is further carried out with intermediate of formula (4'b) or (5'b).

In the next step, intermediate of formula (4'b) or (5'b) is reduced with a suitable reducing agent resulting in intermediate of formula (6c), wherein $R^4$ has the same meaning as that defined above.

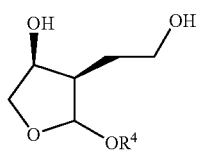

6c

The reduction step can be accomplished using the same reaction conditions as those previously described for the reduction step.

The last step consists of converting intermediate of formula (6c) to the compound of formula (7.3) by a cyclisation reaction. The cyclisation reaction occurs via an intramolecular transacetalisation reaction. Said reaction is preferably performed by treatment of intermediate of formula (6c) with a catalytic amount of a strong acid in water. In a preferred embodiment, the strong acid is selected from group consisting of hydrochloric acid and sulfuric acid.

The preparation of (3S, 3aS, 6aR) hexahydro-furo[2,3-b] furan-3-ol of formula (7.4) can suitably be performed,

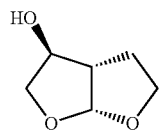

7.4 by following the sequence of reactions described above for the synthesis of compound of formula (7.3) and controlling the conditions of the condensation step, and the nitromethane addition step, such that intermediate of formula (3b) is obtained as the major isomer, by changing for example the type of base used, the solvent and the reaction temperature. After the Nef reaction, the next step consists of isolating intermediates of formula (4b) or (5b) and then reducing said intermediate to obtain intermediate of formula (6d),

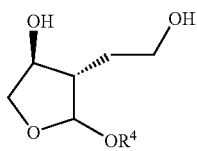

6d which is further cyclised to compound of formula (7.4).

Another aspect of the present invention relates to new intermediates and methods of producing the same. The present invention relates to new intermediates having the formula (3), wherein $P^1$ and $P^2$ are defined as above, $R^2$ is $COOR^3$, and $R^1$ and $R^3$ are defined as above, said intermediates having the formula (3.1).

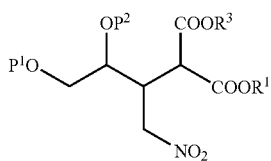

3.1

Said intermediates of formula (3.1) are obtainable by the methods of the present invention.

Also intermediates of formula (3) wherein $R^2$ is hydrogen, said intermediates having the formula (3.2), are deemed novel provided that when $P^1$ and $P^2$ taken together form an isopropylidene, $R^1$ is other than methyl or ethyl.

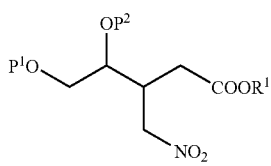

3.2

According to a preferred embodiment the present invention relates to intermediates having the stereochemistry (3a), (3b), (3c) and (3d), wherein $P^1$, $P^2$, $R^1$, $R^2$, $R^3$ have the same meaning as that defined above.

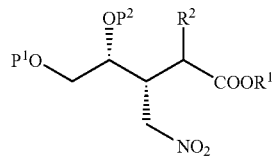

3a

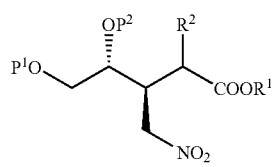

3b

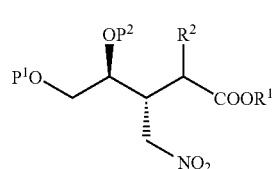

3c

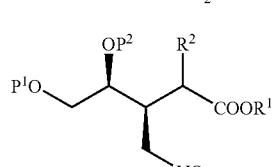

3d

According to a more preferred embodiment the present invention relates to intermediates of formula (3a), (3b), (3c) and (3d), wherein $P^1$, $P^2$ form together a vicinal-diol protecting group, $R^2$ is $COOR^3$, said intermediates having the formula (3a.1), (3b.1), (3c.1) and (3d.1) respectively. Suitably, $R^1$ and $R^3$ each independently are selected from the group consisting of methyl, ethyl, propyl, isopropyl, n-butyl, isobutyl, sec-butyl, tert-butyl and pentyl, more interestingly, $R^1$ and $R^3$ are the same.

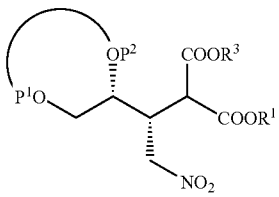

3a.1

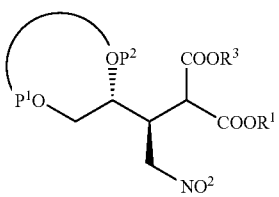

3b.1

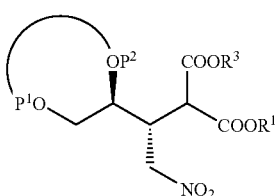

3c.1

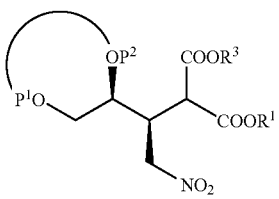

3d.1

In a yet more preferred embodiment the present invention relates to intermediates having the formula (3a.1), (3b.1), (3c.1) and (3d.1), wherein $P^1$ and $P^2$ taken together form a dialkyl methylene, said intermediates having the formula (3a.1a), (3b.1a), (3c.1a) and (3d.1a) repsectively. Suitably, $R^1$ and $R^3$ each independently are selected from the group consisting of methyl, ethyl, propyl, isopropyl, n-butyl, isobutyl, sec-butyl, tert-butyl and pentyl, more interestingly, $R^1$ and $R^3$ are the same. In a more preferred embodiment, $R^1$ and $R^3$ each independently are methyl, ethyl or tert-butyl and more interestingly, $R^1$ and $R^3$ are the same.

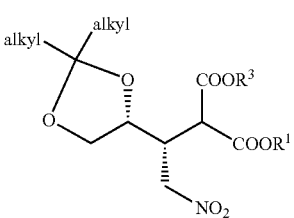

3a.1a

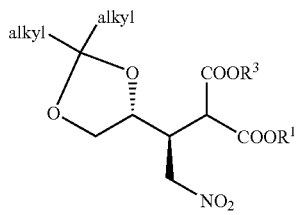

3b.1a

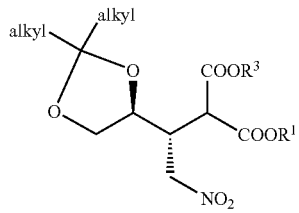

3c.1a

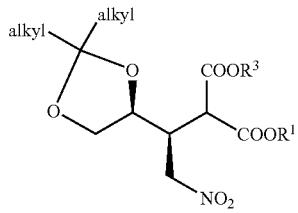

3d.1a

Another preferred embodiment of the present invention relates to intermediates of formula (3a), (3b), (3c) and (3d), wherein $P^1$, $P^2$ form together a vicinal-diol protecting group, $R^2$ is H, said intermediates having the formula (3a.2), (3b.2), (3c.2) and (3d.2) respectively. Suitably, $R^1$ is selected from the group consisting of methyl, ethyl, propyl, isopropyl, n-butyl, isobutyl, sec-butyl, tert-butyl and pentyl.

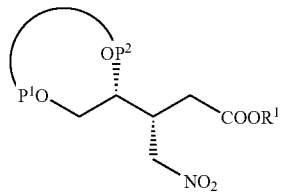

3a.2

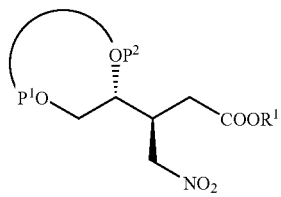

3b.2

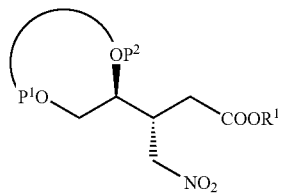

3c.2

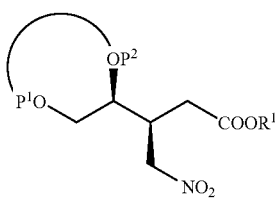
3d.2

In yet another preferred embodiment the present invention relates to intermediates having the formula (3a.2), (3b.2), (3c.2) and (3d.2), wherein $P^1$ and $P^2$ taken together form a dialkyl methylene, said intermediates having the formula (3a.2a), (3b.2a), (3c.2a) and (3d.2a) respectively. Suitably, $R^1$ is selected from the group consisting of methyl, ethyl, propyl, isopropyl, n-butyl, isobutyl, sec-butyl, tert-butyl and pentyl, more interestingly, $R^1$ is methyl, ethyl or tert-butyl.

3a.2a 3b.2a 3c.2a 3d.2a

Intermediates of formula (3c.2a) and (3d.2a) wherein $R^1$ is ethyl have been described in Patrocinio et al., Synthesis (1994), 5, 474–6.

Suitable, in the intermediates of formula (3a.1a), (3b.1a), (3c.1a) and (3d.1a), and (3a.2a), (3b.2a), (3c.2a) and (3d.2a), alkyl is $C_{1-6}$alkyl, preferably, $C_{1-4}$alkyl, and most preferably methyl or ethyl.

In general, the synthesis of the stereoisomeric forms of formula (3a), (3b), (3c) or (3d) can be performed by starting with optically pure intermediate of formula (1a) or (1b) respectively.

Yet another aspect of the invention relates to intermediates of formula (4), (4'), (5) and (5') which are deemed novel. Said intermediates are obtainable by a method according to the invention.

According to a preferred embodiment the present invention relates to intermediates of formula (5a), (5'b), wherein $R^4$ is selected for the group consisting of methyl, ethyl, propyl, isopropyl, n-butyl, isobutyl, sec-butyl, tert-butyl and pentyl. In a more preferred embodiment, $R^4$ is methyl or ethyl.

The synthesis of intermediates of formula (5a) or (5'b) are conveniently carried by starting with optically pure intermediate of formula (1a) or (1b) respectively.

The compounds of formula (7) find their particular use in the preparation of a medicament. According to a preferred embodiment, the present compounds of formula (7) are used as precursor in the preparation of anti-viral drugs, in particular anti-HIV drugs, more in particular HIV protease inhibitors.

The compound of formula (7.1) and all intermediates leading to the formation of said stereoisomerically pure compound are of particular interest in preparing HIV protease inhibitors as disclosed in WO 95/24385, WO 99/65870, WO 00/47551, WO 00/76961 and U.S. Pat. No. 6,127,372, WO 01/25240, EP 0 715 618 and WO 99/67417 all incorporated herein by reference, and in particular, the following HIV-protease inhibitors.

[(1S,2R)-2-hydroxy-3-[[(4-methoxyphenyl)sulfonyl](2-methylpropyl)amino]-1-(phenyl-methyl)propyl]-carbamic acid (3R,3 aS,6aR)-hexahydrofuro[2,3-b]furan-3-yl ester (HIV protease inhibitor 1);

[(1S,2R)-3-[[(4-aminophenyl)sulfonyl](2-methylpropyl) amino]-2-hydroxy-1-(phenyl-methyl)propyl]-carbamic acid (3R,3aS,6aR)-hexahydrofuro[2,3-b]furan-3-yl ester (HIV protease inhibitor 2);

[(1S,2R)-3-[(1,3-benzodioxol-5-ylsulfonyl)(2-methylpropyl)amino]-2-hydroxy-1-(phenylmethyl)propyl]-carbamic acid (3R,3aS,6aR)-hexahydrofuro[2,3-b]furan-3-yl ester (HIV protease inhibitor 3), or any pharmaceutically acceptable addition salt thereof.

Thus, the present invention also relates to HIV protease inhibitors 1, 2, 3 or any pharmaceutically acceptable salt or prodrug thereof, obtained by using a compound of formula (7.1) prepared according to the present invention in the chemical synthesis of said HIV protease inhibitors. Such chemical synthesis is disclosed in the art, for instance in WO 01/25240, EP 0 715 618 and WO 99/67417.

The following examples are meant to be illustrative of the present invention. These examples are presented to exemplify the invention and are not to be construed as limiting the invention's scope.

EXPERIMENTAL SECTION

General Procedures:

Proton NMR spectra were recorded on a Bruker Avance DPX 400 MHz NMR spectrometer. Proton chemical shifts are reported in ppm (δ) relative to internal tetramethylsilane (TMS, δ0.0). Analytical thin-layer chromatography (TLC) was performed using silica gel 60 A $F_{254}$ precoated plates (0.25 mm thickness). TLC Rf values are reported. Visualization was accomplished by staining with a solution of KMnO$_4$ in acetone or with a solution of vaniline in a 1/1 mixture of water and concentrated sulfuric acid. Analytical gas chromatography (GC) was performed using a DB-XLB column. Analytical chiral GC was performed using a cyclodex-β column. Detection on both columns was accomplished by employing a flame ionization detector. All solvents and reagents were retrieved by commercial suppliers and used without any treatment or purification prior to their use. L-5,6-O-Isopropylidene-gulono-1,4-lactone was prepared from L-ascorbic acid according to C. Hubschwerlen *Synthesis* 1986, 962–964.

(determined by $^1$H NMR). The $^1$H NMR spectrum was consistent with that of the desired structures.

Synthesis of I.4

Compound (I.3, 0.1 mol, 20 g, E/Z: 96/4) and nitromethane (0.11 mol, 6.7 g) were dissolved in acetonitrile (200 ml) and cooled to 0° C. A solution of 1,8-diazabicyclo-[5.4.0]undec-7-ene (0.15 mol, 22.8 g) in acetonitrile (50 ml) was added dropwise over 5 minutes. The reaction mixture was stirred overnight at room temperature. Then, most the solvent was removed under reduced pressure. The oily residue was diluted with water (200 ml) and extracted with

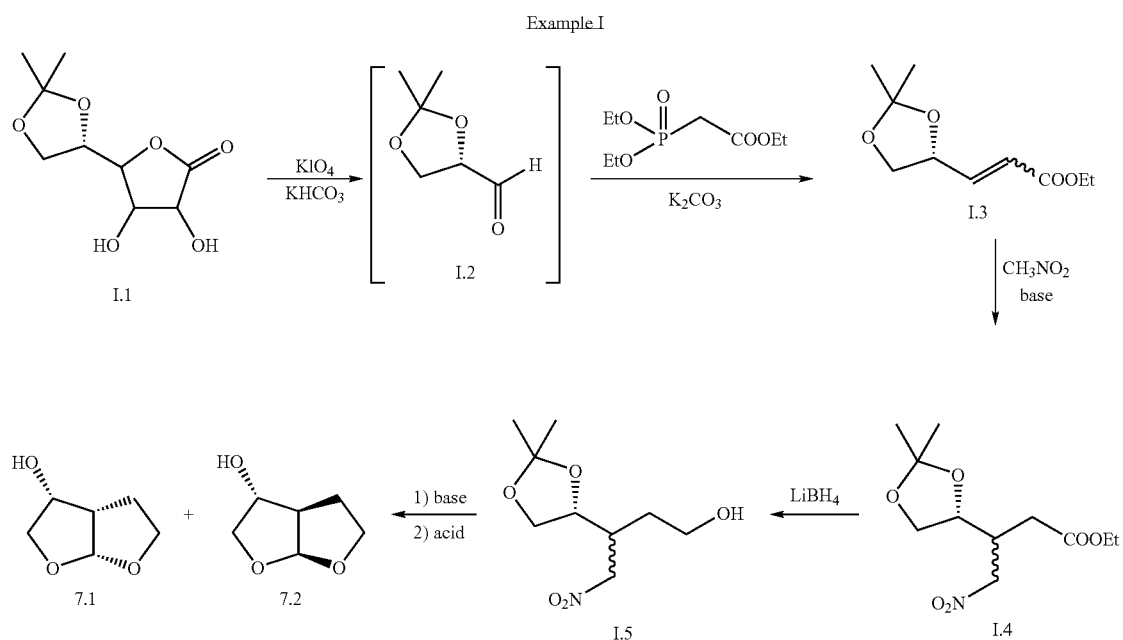

Example I

Synthesis of I.3

Potassium periodate (0.25 mol, 57.5 g) and potassium hydrogen carbonate (0.25 mol, 25 g) were slurried in water (100 ml) and cooled to 0° C. L-5,6-O-Isopropylidene-gulono-1,4-lactone (I.1, 0.12 mol, 26 g) was dissolved in tetrahydrofuran (100 ml) and water (100 ml) and added dropwise over 20 minutes to the periodate solution at 0° C. After addition, the mixture was stirred at room temperature for 4 hours and then cooled to 0° C. The solids were removed by filtration and washed with tetrahydrofuran (100 ml). The combined organic filtrates containing 2,3-O-isoproylideneglyceralde-hyde (I.2) were used without evaporation of the solvents in the next step. Triethylphosphonoacetate (0.114 mol, 32 g) was added to the combined filtrates at 0° C. Potassium carbonate (0.6 mol, 83 g) was dissolved in water (160 ml) and added dropwise over 1 hour at 0° C. to the reaction mixture. The two-phase solution was stirred for 4 hours. The organic phase was separated and the aqueous phase was extracted with ethyl acetate (3×100 ml). The combined organic phases were washed with water (2×100 ml) and the solvent was evaporated to give a pale yellow oil. This crude oil was filtered through silica, eluting with n-hexane/ethyl acetate (10/90) to yield compound (I.3, 14.3 g, yield=60%) as an E/Z mixture in a ratio 96/4 ethyl acetate (3×200 ml). The combined organic layers were washed with 5% hydrochloric acid (200 ml) and then with a saturated sodium hydrogen carbonate solution. Drying over MgSO$_4$ and evaporation under reduced pressure afforded intermediate (I.4, 9 g, yield=34%) in a syn/anti ratio of 75/25 (determined by $^1$H NMR). The $^1$H NMR spectrum was consistent with that of the desired structures.

Synthesis of I.5

A solution of compound (I.4, 0.03 mol, 7.8 g, syn/anti: 75/25) in tetrahydrofuran (100 ml) was cooled to 0° C. Lithium borohydride (0.045 mol, 1 g) was added in portions over 30 minutes and the mixture was stirred overnight at room temperature. The reaction was quenched by the slow addition of a saturated ammonium chloride solution (100 ml) under cooling (0° C.), extracted with ethyl acetate (10×50 ml) and dried over MgSO$_4$. Evaporation under reduced pressure afforded compound (I.5, 6.02 g, yield=92%) as an oil. The $^1$H NMR spectrum was consistent with that of the desired structures.

Synthesis of hexahydro-furo[2,3-b]furan-3-ol (7.1 and 7.2):

To a stirred solution of compound (I.5, 0.011 mol, 2.4 g, syn/anti mixture) in isopropanol (20 ml), potassium tert-butoxide (0.0132 mol, 1.5 g) was added portionwise over 30 minutes at room temperature. The basic solution was transferred to an addition funnel and added dropwise over 10 minutes to a cooled (0° C.) vigorously stirred mixture of concentrated (37%) hydrochloric acid (0.0275 mol, 2.3 ml) in isopropanol (20 ml). The reaction mixture was stirred for 2 hours at room temperature, then triethylamine (0.022 mol, 2.2 g) was added dropwise causing Et$_3$N.HCl salts to precipitate. The reaction mixture was diluted with ethyl acetate (50 ml) and filtered to remove the salts. The solvent was evaporated under reduced pressure. The residue was diluted with ethyl acetate (50 ml) causing more Et$_3$N.HCl salts to precipitate. The salts were removed by filtration and the solvent was evaporated under reduced pressure. The residual oil was further purified by silica gel plug filtration with ethyl acetate as eluent to afford a mixture of compounds (7.1/7.2, 1.03 g, yield=72%) in a ratio of 78/22 (determined by $^1$H NMR). Analytical samples of the pure compounds (7.1, Rf$_{7.1}$=0.27) and (7.2, Rf$_{7.2}$=0.15) were obtained by means of silica gel chromatography using ethyl acetate as the solvent.

(3R,3aS,6aR)-Hexahydro-furo[2,3-b]furan-3-ol (7.1): $^1$H NMR (400 MHz, CDCl$_3$): δ 1.80–1.91 (1H, m), 2.28–2.34 (1H, m), 2.83–2.89 (1H, m), 3.11 (1H, broad s), 3.35–3.59 (1H, m), 3.85–3.98 (3H, m), 4.38–4.45 (1H, m), 5.66 (1H, d, J=5.2 Hz).

(3R,3aR,6aS)-Hexahydro-furo[2,3-b]furan-3-ol (7.2): $^1$H NMR (400 MHz, CDCl$_3$): δ 1.68–1.75 (1H, m), 2.12–2.23 (1H, m), 2.42 (1H, broad s), 2.79–2.85 (1H, m,), 3.81–3.91 (3H, m), 3.964.01 (1H, m), 4.23 (1H, m), 5.89 (1H, d, J=4.9 Hz).

The reaction mixture was stirred overnight at room temperature, then transferred into an addition funnel and added dropwise over 30 minutes to a cooled (0° C.) vigorously stirred solution of concentrated sulfuric acid (0.03 mol, 0.8 ml) in ethanol (10 ml). After stirring at room temperature overnight, the reaction mixture was diluted with water (100 ml) and extracted with dichloromethane (3×50 ml). The combined organic phases were washed with a saturated sodium hydrogen carbonate solution (100 ml), dried over MgSO$_4$ and evaporated under reduced pressure to afford a crude mixture of products (II.3/II.3°, 1.27 g, yield=58%) as an oil. Using $^1$H NMR analysis, compound II.3 was identified as the major component in the product mixture. The crude product mixture was used as such in the next step.

Synthesis of (7.1) and (7.2) from Crude (II.3/II.3'):

The crude product mixture (II.3/II.3') (0.006 mol, 1.27 g) was dissolved in tetrahydrofuran (20 ml) and cooled to 0° C. Lithium borohydride (0.009 mol, 200 mg) was added in portions over 5 minutes and the mixture was stirred overnight at room temperature. The solvent was evaporated under reduced pressure and the residue was dissolved in isopropanol (25 ml). Concentrated (37%) hydrochloric acid (1 ml) was added dropwise and the mixture was stirred for 4 hours at room temperature. Then, triethylamine (5 ml) was added dropwise causing Et$_3$N.HCl salts to precipitate. The reaction mixture was diluted with ethyl acetate (100 ml) and filtered to remove the salts. The solvent was evaporated under reduced pressure. The residue was diluted with ethyl acetate (100 ml) causing more Et$_3$N.HCl salts to precipitate.

Example II

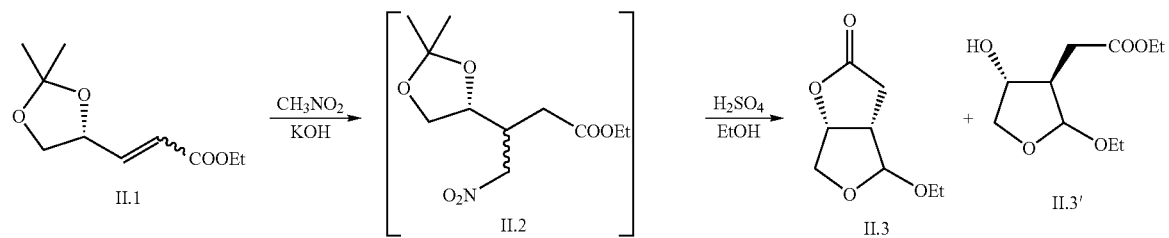

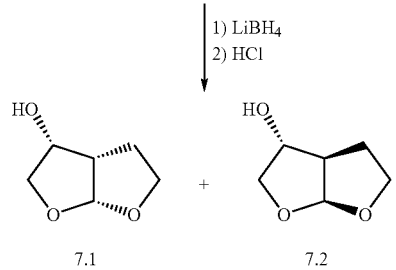

Synthesis of II.3 and II.3'

A solution of nitromethane (0.011 mol, 0.67 g) in ethanol (5 ml) was cooled to 0° C. 1,8-Diazabicyclo[5.4.0]undec-7-ene (0.015 mol, 2.3 g) in ethanol (5 ml) was added dropwise and the reaction was stirred for 30 minutes. Compound (II.1, 0.01 mol, 2 g, E/Z=96/4) was dissolved in ethanol (5 ml) and added dropwise to the solution at 0° C.

The salts were removed by filtration and the solvent was evaporated under reduced pressure. The residual oil was further purified by silica gel plug filtration with ethyl acetate as eluent to afford a mixture of compounds (7.1/7.2, 0.68 g, yield 87%) in a ratio of 87/13 (determined by $^1$H NMR). The $^1$H NMR spectrum was consistent with that of the desired structures.

Example III

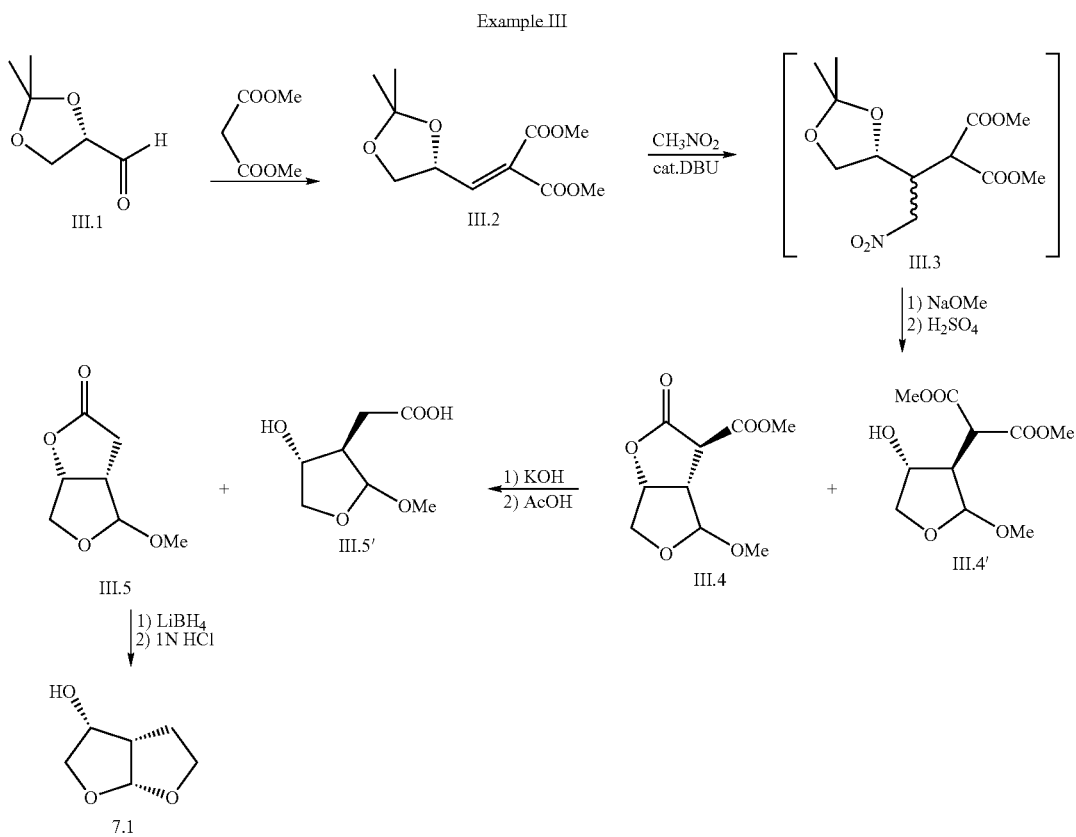

Synthesis of III.2

2,3-O-Isoproylidene-glyceraldehyde (III.1, 0.1 mol, 65 g of a 20% w/w solution of III.1 in tetrahydrofuran) was mixed with dimethyl malonate (0.15 mol, 19.8 g), acetic anhydride (0.3 mol, 30.6 g) and pyridine (0.05 mol, 3.95 g) and stirred at room temperature overnight. The reaction mixture was evaporated under reduced pressure. The residual oil was diluted with dichloromethane (200 ml), washed with a saturated sodium hydrogen carbonate solution (3×100 ml), dried over MgSO$_4$ and evaporated under reduced pressure. Fractionated distillation afforded (III.2, bp: 88–94° C./0.03 mmHg, 14.2 g, yield=58%, purity by GC: 83%). TLC (ethyl acetate/hexane 20/80): Rf$_{(III.2)}$=0.43 (KMnO$_4$ in acetone). $^1$H NMR (400 MHz, CDCl$_3$): δ 1.39 (3H, s), 1.45 (3H, s), 3.71–3.75 (1H, m), 3.81 (3H, s), 3.83 (3H, s), 4.25–4.29 (1H, m), 4.90–4.95 (1H, m), 7.04 (1H, d, J=7.1 Hz).

Synthesis of (III.3):

To a stirred solution of (111.2, 2 mmol, 490 mg) in methanol (20 ml), was added first nitromethane (2.2 mmol, 134 mg) and then 1,8-diazabicyclo[5.4.0]undec-7-ene (0.5 mmol, 76 mg) and the reaction mixture was stirred at room temperature for 3 hours. The solvents were evaporated under reduced pressure. The residual oil was diluted with a saturated ammonium chloride solution, extracted with dichloromethane, dried over MgSO$_4$ and evaporated under reduced pressure to afford crude (111.3) as a syn/anti mixture in ratio's ranging from 90/10 to 97/3 (determined by $^1$H NMR). TLC (ethyl acetate/hexane 20/80): Rf$_{(III.3)}$=0.29 (KMnO$_4$ in acetone): the syn/anti-(III.3) isomers do not appear as separated spots on TLC. The structure of compound syn-(III.3) was identified from the $^1$H NMR spectrum of the crude reaction mixture: syn-(III.3): $^1$H NMR (400 MHz, CDCl$_3$): δ 1.23 (3H, s), 1.31 (3H, s), 3.13 (1H, ~quintet, J=5.5 Hz), 3.55 (1H, d, J=5.5 Hz), 3.66–3.69 (overlapping, 1H, m), 3.68 (3H, s), 3.70 (3H, s), 4.05 (1H, dd, J$_1$=8.8 Hz, J$_2$=6.7 Hz), 4.22 (1H, ~q, J=5.9 Hz), 4.60 (1H, dd, J=14.8 Hz, J$_2$=4.8 Hz), 4.67 (1H, dd, J$_1$=14.8 Hz, J$_2$=5.9 Hz).

Synthesis of (III.4/III.4') from (III.2):

To a stirred solution of (III.2, 0.05 mol, 12.2 g) in methanol (50 ml), was added first nitromethane (0.055 mol, 3.36 g) and then 1,8-diazabicyclo[5.4.0]undec-7-ene (5 mmol, 760 mg) and the reaction mixture was stirred at room temperature for 4 hours. The reaction mixture was cooled to 0° C. and a solution of sodium methoxide 2N in methanol (0.05 mol, 25 ml) was added dropwise over 30 minutes. The mixture was then transferred to an addition funnel and added dropwise over 45 minutes to a cooled vigorously stirred solution of concentrated sulfuric acid (0.125 mol, 12 g) in methanol (25 ml), keeping the internal temperature <10° C. During the addition, a white precipitate was formed and the suspension was stirred overnight at room temperature. The reaction mixture was evaporated to half of the original volume and then slowly poured into a cooled saturated sodium hydrogen carbonate solution (200 ml), keeping the internal temperature <10° C. The aqueous phase was extracted with ethyl acetate (4×50 ml), the combined extracts were washed with water (50 ml) and evaporated to afford a mixture of crude compounds (III.4/III.4', 8.37 g, yield=78%) as an oil. The $^1$H NMR spectrum of the crude reaction mixture showed compound (111.4) to be the major reaction product. An analytical sample of compound (III.4)

was obtained by flash chromatography on silica gel, eluting with ethyl acetate/hexane 50/50. TLC (ethyl acetate/hexane 50/50): Rf$_{(III.4)}$=0.45 (KMnO$_4$ in acetone). (III.4): $^1$H NMR (400 MHz, CDCl$_3$): δ 3.33 (3H, s), 3.39 (1H, dd, J=7.0 Hz J$_2$=4.4 Hz), 3.58 (1H, d, J=4.4 Hz), 3.82 (3H, s), 3.97 (1H, dd, J$_1$=11 Hz, J$_2$=3.9 Hz), 4.10 (1H, d, J=11 Hz), 4.95 (1H, s), 5.23 (1H, dd, J=7.0 Hz, J$_2$=3.9 Hz).

Synthesis of (III.5):

Potassium hydroxide (0.025 mol, 1.42 g) was dissolved in methanol (10 ml) and water (2 ml). A solution of crude (III.4/III.4', 0.023 mol, 5.2 g) in methanol (10 ml) was added and the reaction mixture was heated under reflux for 2 to 3 hours. TLC analysis indicated the complete conversion of all starting material (III.4/III.4') and the reaction mixture was concentrated under reduced pressure to ⅕ of the original volume. The residual solution was mixed with acetic acid (10 ml) and stirred at room temperature for 2 hours. Then, the reaction mixture was diluted with water (20 ml) and extracted with ethyl acetate (3×20 ml). The combined organic layers were washed with a saturated sodium hydrogen carbonate solution (20 ml), dried over MgSO$_4$ and evaporated under reduced pressure to afford compound (III.5, 2.35 g, yield=65%) as a solid. An analytical sample of compound (III.5) was obtained by recrystallisation from isopropanol to afford pure compound (III.5) as colorless needles. TLC (EtOAc): Rf$_{(III.5)}$=0.49. (III.5): $^1$H NMR (400 MHz, CDCl$_3$): δ 2.51 (1H, dd, J$_1$=18.6 Hz, J$_2$=4.0 Hz), 2.84 (1H, dd, J=18.6 Hz, J$_2$=11.3 Hz), 3.00–3.06 (1H, m), 3.33 (3H, s), 3.95 (1H, dd, J$_1$=10.9 Hz, J$_2$=3.9 Hz), 4.10 (1H, d, J=10.9 Hz), 4.88 (1H, s), 5.14 (1H, dd, J$_1$=7.0 Hz, J$_2$=3.9 Hz).

Synthesis of (7.1) from (III.5):

To a cooled (0° C.) solution of compound (III.5, 0.011 mol, 1.88 g) in tetrahydrofuran (20 ml), lithium borohydride (0.017 mol, 370 mg) was added in portions over 10 minutes. The suspension was stirred overnight at room temperature until TLC analysis indicated the complete conversion of starting material (III.5). Then, the reaction mixture was cooled on ice and quenched by addition of water (5 ml). The reaction mixture was evaporated under reduced pressure (bath temperature=40° C., P=200 mbar) until most of the tetrahydrofuran was evaporated and the residual aqueous solution was acidified with 2N hydrochloric acid to pH=0–1. The reaction mixture was stirred for 1 hour at room temperature, saturated with sodium chloride and extracted with ethyl acetate (5×20 ml). The combined organic layers were dried over MgSO$_4$ and evaporated under reduced pressure to give compound (7.1, 1.01 g, yield=71%) as a colorless oil. The structure of (7.1) was confirmed by the $^1$H NMR spectrum. The enantiomeric purity of compound (7.1) was determined by GC analysis of its acetate. Therefore, compound (7.1, 0.5 g) was mixed with acetic anhydride (2 g) and N,N-dimethyl-4-aminopyridine (100 mg) and stirred at room temperature overnight. The reaction mixture was diluted with hexane (50 ml) and washed with a saturated hydrogen carbonate solution (2×50 ml) and then with water (50 ml). Chiral GC analysis of the hexane solution allowed to determine the enantiomeric excess of compound (7.1) to be >99%.

Example IV

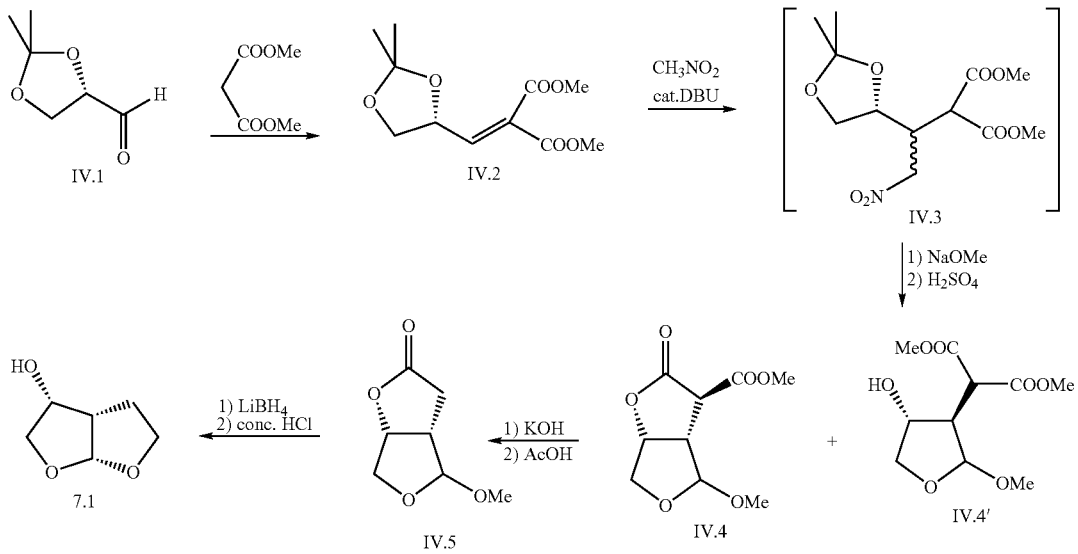

Synthesis of (IV.2)

2,3-O-Isoproylidene-glyceraldehyde (IV.1, 1654 mol, 1075 kg of a 20% w/w solution of (IV.1) in tetrahydrofuran) was mixed with dimethyl malonate (1 equiv., 1654 mol, 218 kg) and stirred at 20° C. for 3 hours. Pyridine (0.5 equiv., 827 mol, 65.5 kg) was added and the reaction mixture was heated to 45° C. At this temperature, a solution of acetic anhydride (3 equiv, 4962 mol, 506 kg) in tetrahydrofuran (506 kg) was added over a period of 4 hours. After heating for 12 hours at 45° C., most of the solvent (1200 kg) was removed by vacuum evaporation and the residual oil was diluted with toluene (2500 kg). The organic solution was added over a period of 2 hours to a vigorously stirred aqueous sodium hydrogen carbonate suspension previously prepared by mixing solid sodium hydrogen carbonate (190 kg) with 1N sodium hydrogen carbonate (1760 kg). After phase separation, the aqueous phase was removed and the organic phase was washed with 1N sodium hydrogen carbonate (1760 kg). Then, most toluene was evaporated under reduced pressure to a residual amount of about 450 kg. Further removal of toluene and solvent switch to methanol was performed by azeotropic distillation with methanol by repeated (twice) addition of methanol (500 kg) and evaporation of the same amount (500 kg) under reduced pressure. Finally, methanol (830 kg) was added to yield intermediate IV.2 (1280 kg of a 23.6% solution in methanol). Intermediate IV.2 was used as such in the next step.

Synthesis of (IV.4/IV.4') from (IV.2):

Intermediate (IV.2) (503 mol, 520 kg of a 23.6% w/w of IV.2 in methanol) was mixed with nitromethane (1.1 equiv., 553 mol, 62 kg of a 55% w/w of nitromethane in methanol) and to the stirred reaction mixture 1,8-diazabicyclo[5.4.0]undec-7-ene (0.1 equiv., 50.3 mol, 7.6 kg) was added over a period of 30 minutes under cooling, keeping the internal temperature <25° C. Stirring was continued at room temperature for 3 hours. The reaction mixture was cooled to 0° C. and sodium methoxide 2N in methanol (1.1 equiv., 553 mol, 100 kg of a 30% w/w solution of sodium methoxide in methanol) was added dropwise over 30 minutes, keeping the internal temperature at 0° C. After 30 minutes at 0° C., the reaction mixture was dosed over a period of 1 hour to a cooled (0° C.), vigorously stirred solution of concentrated sulfuric acid (2.5 equiv. 1258 mol, 128 kg of 96% sulfuric acid) in methanol (200 kg), keeping the internal temperature <10° C. The reaction mixture was further cooled to 0° C. and added to a vigorously stirred, cooled (0° C.) biphasic system of ethyl acetate (450 kg) and 1N sodium hydrogen carbonate (1.9 equiv., 1905 kg) over a period of 1 hour, keeping the internal temperature <15° C. The reaction mixture was filtered to remove most of the precipitated sodium sulfate. After phase separation, the organic phase was collected and the aqueous phase was extracted four times with ethyl acetate (total amount of ethyl acetate: 2250 kg). The collected organic phases were washed with brine (300 kg of a 23% w/w sodium chloride solution) and evaporated under reduced pressure to a residual amount of 750 kg (containing ca. 66 kg of intermediate IV.4). Intermediate IV.4 was used as such in the next step.

Synthesis of (IV.5) from (IV.4)

To a stirred solution of (IV.4) (750 kg of a solution ca. 66 kg IV.4 in methanol) was added water (38 kg) and potassium hydroxide (553 mol, 68 kg of 45% aqueous potassium hydroxide) and the reaction mixture was heated to reflux for 2 hours. After rapid cooling to 35° C., acetic acid (830 mol, 46 kg of 96% acetic acid) was added and the reaction mixture was evaporated under reduced pressure over a period of 10 hours to a residual amount of ca. 200 kg. After cooling to room temperature, more acetic acid (354 kg) was added over a period of 1 hour. After stirring for 2 hour at room temperature, most acetic acid was removed by vacuum evaporation over a period of 10 hours to a residual amount of ca. 250 kg. Water (800 kg) was added and the aqueous solution was extracted three times with ethyl acetate (3×700 kg). The combined organic layers were washed twice with 1N sodium hydrogen carbonate (2×586 kg). A third washing with 1N sodium hydrogen carbonate was performed with pH control; 1N sodium hydrogen carbonate was added until a pH of 6.8–7.2 (ca. 410 kg 1N sodium hydrogen carbonate was used). A solvent switch from ethyl acetate to isopropanol was performed by subsequent evaporation of the organic solution under reduced pressure to a residual amount of 200 kg, addition of isopropanol (350 kg), evaporation of the organic solution under reduced pressure to a residual amount of 200 kg and addition of isopropanol (350 kg). The reaction mixture was heated to 60–70° C. and isopropanol was further evaporated at that temperature under reduced pressure to a residual amount of ca. 144 kg. After filtration, the reaction mixture was cooled to 0° C. over a period of 4–5 hours, allowing crystallisation of intermediate (IV.5). Filtration and drying (vacuum drying at 40° C.) of the crystals yielded intermediate (IV.5) (27 kg). Intermediate IV.5 was used as such in the next step.

Synthesis of (7.1):

To a solution of intermediate (IV.5) (180 mol, 30 kg) in tetrahydrofuran (160 kg), lithium borohydride (1.1 equiv., 198 mol, 43.1 kg of a solution of 10% lithium borohydride in tetrahydrofuran) was added over 30 minutes. The reaction mixture was heated to 50° C. over a period of 1 hour and stirred at that temperature for 2 hours. The obtained suspension was cooled to −10° C. and hydrochloric acid (1.2 equiv. relative to LiBH$_4$, 238 mol, 27.2 kg of 32% hydrochloric acid) was dosed over a period of 4 hours, keeping the internal temperature <−5° C. After stirring at −10° C. for an additional 2 hours, triethylamine (1.1 equiv. relative to HCl, 261 mol, 26.5 kg) was added over a period of 1 hour, while maintaining the internal temperature <0° C. A solvent switch to ethyl acetate was performed by distillation of the solvents under atmospheric pressure to a residual amount of ca. 100 kg, addition of ethyl acetate (360 kg) and further distillation of the tetrahydrofuran/ethyl acetate solvent mixture with continues addition of ethyl acetate to maintain a constant volume. This procedure was continued until a tetrahydrofuran/ethyl acetate ratio of 4:1 (checked by gas chromatography). The resulting mixture was cooled to 0° C., filtered and the filter cake was washed with two portions of ethyl acetate (2×30 kg). The collected filtrates were evaporated to yield compound (7.1) (18 Kg). The identity of compound 7.1 was confirmed using HPLC, NMR and chiral gas chromatography using reference samples from Example III.

What is claimed is:

1. A method for the synthesis of hexahydro-furo[2,3-b]furan-3-ol of formula (7) starting from an intermediate of formula (1) wherein P$^1$ and P$^2$ represent each independently a hydrogen, a hydroxy-protecting group or may together form a vicinal-diol protecting group,

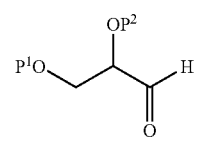

transforming said intermediate of formula (1) into a nitromethane derivative of formula (3) wherein R$^1$ represents alkyl, aryl or aralkyl, R$^2$ represents hydrogen or C(=O)OR$^3$, R$^3$ represents alkyl, aryl or aralkyl, or R$^3$, if present, and R$^1$ taken together with the atoms to which they are attached may form a 6 to 8-membered cyclic group which may be optionally substituted with alkyl, aralkyl, or aryl,

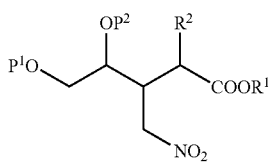

3 subsequently transforming said nitromethane derivative into a tetrahydrofuran derivative of formula (6) wherein OR$^4$ represents an alcoholate,

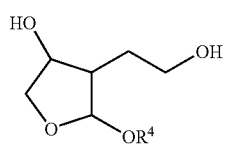

6 and then transforming the intermediate of formula (6) into hexahydro-furo[2,3-b]furan-3-ol of formula (7) by way of an intramolecular cyclisation reaction

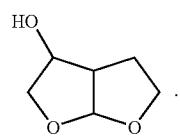

7

.

2. A method according to claim 1 wherein the intermediate of formula (3) is transformed into an intermediate of formula (6) by making use of a Nef reaction.

3. A method according to claim 1 for the synthesis of hexahydro-furo[2,3-b]-furan-3-ol of formula (7), which comprises the steps of:

a) condensing an intermediate of formula (1)

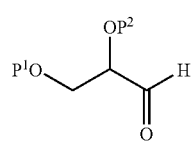

1 resulting in an α,β-unsaturated ester of formula (2),

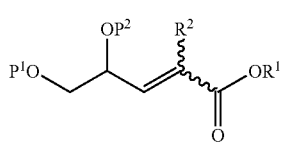

2 b) reacting said ester of formula (2) with nitromethane resulting in an intermediate of formula (3),

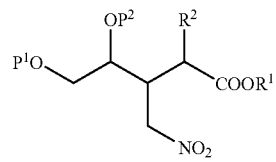

3 c) submitting said intermediate of formula (3) to a Nef reaction leading to intermediates of formula (4) and (4')

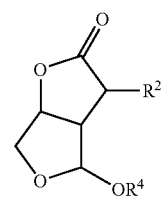

4

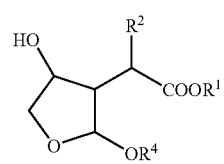

4' d) transforming said intermediates of formula (4) and (4') into an intermediate of formula (6) and,

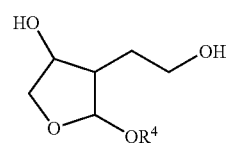

6 e) converting intermediate of formula (6) to the compound of formula (7) by an intramolecular cyclisation reaction.

4. A method according to claim 1 for the synthesis of hexahydro-furo[2,3-b]furan-3-ol of formula (7), which comprises the steps of:

a) condensing an intermediate of formula (1) with CHR$^2$R$^5$—C(=O)—OR$^1$ wherein R$^5$ represents a hydrogen, a carboxylic ester, a phosphonium salt or a phosphonate ester,

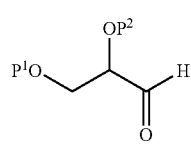

1 resulting in an α,β-unsaturated ester of formula (2)

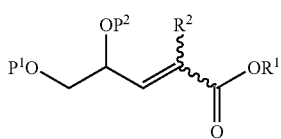

b) reacting said ester of formula (2) with nitromethane resulting in an intermediate of formula (3),

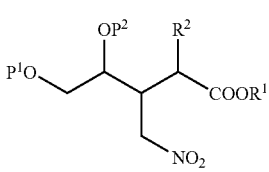

c) submitting said intermediate of formula (3) to a Nef reaction by treating it with a base and subsequently with a strong acid resulting in a mixture of intermediates of formula (4) and (4'),

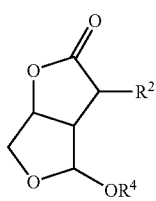

d) only in case $R^2$ is different from hydrogen, decarboxylating the intermediates of formula (4) and (4') thus forming intermediates of formula (5) and (5') respectively,

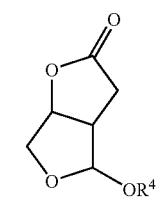

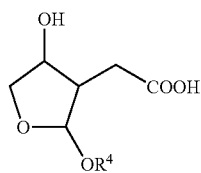

e) reducing intermediates of formula (4) and (4'), or intermediates of formula (5) and (5') with a suitable reducing agent resulting in intermediate of formula (6) and,

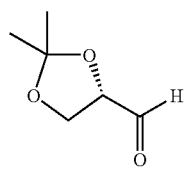

f) converting intermediate of formula (6) to the compound of formula (7) by an intramolecular cyclisation reaction.

5. A method according to claim 1 for the synthesis of hexahydro-furo[2,3b]furan-3-ol of formula (7.1) starting from an intermediate of formula (1), wherein $P^1$ and $P^2$ taken together form an isopropylidene,

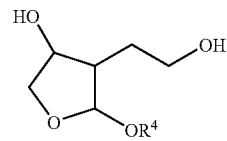

condensing said intermediate of formula (1) resulting in an intermediate of formula (2), wherein $P^1$ and $P^2$ taken together form an isopropylidene, $R^2$ represents —C(=O)OR$^3$, wherein $R^3$ is methyl and $R^1$ is methyl,

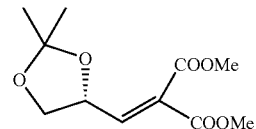

reacting said ester of formula (2) into a nitromethane derivative of formula (3) wherein $P^1$ and $P^2$ taken together form an isopropylidene, $R^2$ represents —C(=O)OR$^3$, wherein $R^3$ is methyl, and $R^1$ is methyl,

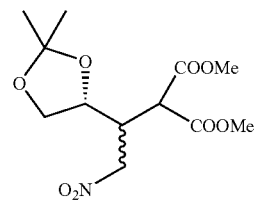

transforming said intermediate of formula (3) using a base and subsequently an acid to yield intermediates of formula (4) and (4'), wherein $R^2$ represents —C(=O)OR$^3$, wherein $R^3$ is methyl, $R^1$ is methyl and $R^4$ is methyl,

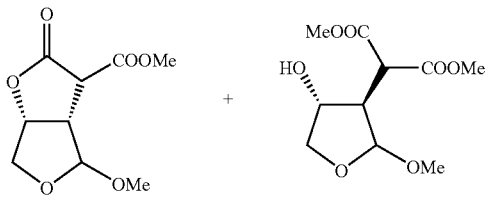

decarboxylating intermediates of formula (4) leading to an intermediate of formula (5), wherein $R^4$ is methyl,

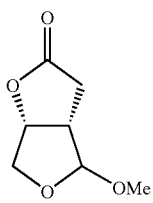

reducing said intermediate of formula (5) with a suitable reducing agent resulting in an intermediate of formula (6), wherein $R^4$ is methyl,

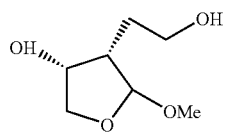

transforming the intermediate of formula (6) into compound 7.1 by way of intramolecular cyclization reaction

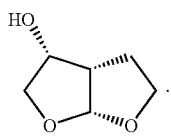

7.1

6. A method according to claim 3 wherein intermediate of formula (3) is submitted to a Nef reaction using acidic quenching while keeping the temperature below −10° C. during said quenching.

7. A method according to claim 4 wherein the decarboxylation of intermediates of formula (4) and (4') is performed in a buffered aqueous solution.

8. A method according to claim 3 wherein intermediate (6) is prepared via reduction of intermediates of formula (4) and (4') or intermediates of formula (5) and (5') using lithium borohydride in tetrahydrofuran or $NaBH_4$ in the presence of LiCl.

9. A method according to claim 3 wherein the cyclisation of intermediate of formula (6) to the compound of formula (7) is performed by adding a strong acid to the reaction mixture containing intermediate of formula (6).

10. A method according to claim 9 wherein the cyclisation reaction is performed at a temperature lower then 5° C.

11. A method according to claim 10 wherein the temperature of the reaction mixture while adding the strong acid to the reaction mixture remains lower than −5° C.

12. A method according to claim 1 wherein an intermediate of formula (3) is prepared by a process comprising the steps of first condensing an intermediate of formula (1) with nitromethane, resulting in an intermediate of formula (8) and secondly, reacting said intermediate of formula (8) with $CHR^2R^8$—$C(=O)$—$OR^1$ wherein $R^8$ is hydrogen or a carboxylic ester

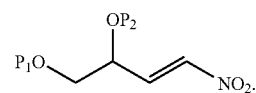

8

13. A method according to claim 12 wherein the carboxylic ester is defined as $C(=O)$—$OR^1$.

14. A method according to claim 1 wherein an intermediate of formula (6) is prepared by a process comprising the steps of first reducing intermediate of formula (3) wherein $R^2$ is hydrogen with a suitable reducing agent, resulting in an intermediate of formula (9) and secondly submitting the obtained intermediate of formula (9) to a Nef reaction by treatment with a base and then with a strong acid

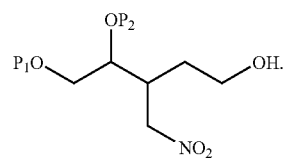

9

15. A method according to claim 1 wherein hexahydrofuro[2,3-b]furan-3-ol of formula (7) is isolated by adding a small excess of a tertiary amine, followed by the removal of water and removal of formed salts.

16. A method according to claim 1 wherein $R^1$ and $R^3$ each independently are $C_{1-6}$alkyl, aryl or aryl$C_{1-6}$alkyl or together with the atoms to which $R^1$ and $R^3$ are attached form a 6 to 8-membered cyclic group optionally substituted with $C_{1-6}$alkyl, aryl or aryl$C_{1-6}$alkyl, and wherein $R^4$ is $C_{1-6}$alkyl.

17. A method according to claim 1 wherein $R^1$, $R^3$ and $R^4$ each independently are methyl, ethyl, propyl, isopropyl, n-butyl, isobutyl, sec-butyl, tert-butyl or pentyl.

18. A method according to claim 1 wherein $P^1$ and $P^2$ together form an acid labile vicinal-diol protecting group.

19. A method according to claim 1 wherein $P^1$ and $P^2$ is a dialkyl methylene radical.

20. A method according to claim 4 wherein $R^5$ is hydrogen, $R^1O$—$C(=O)$—, $(R^6)_3P$= wherein $R^6$ is alkyl, aryl or aralkyl, or $(R^7O)_2P(=O)$— wherein $R^7$ is alkyl, aryl, aralkyl.

21. An intermediate having the formula (3),

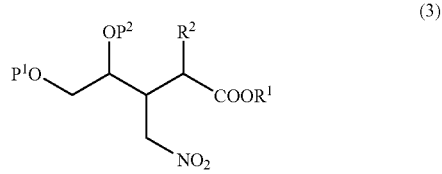

(3)

wherein P¹ and P² represent each independently a hydrogen, a hydroxy-protecting group or may together form a vicinal-diol protecting group, R¹ represents alkyl, aryl or aralkyl, R² represents hydrogen or C(=O)OR³, R³ represents alkyl, aryl or aralkyl, or R³, if present, and R¹ taken together with the atoms to which they are attached may form a 6 to 8-membered cyclic group which may be optionally substituted with alkyl, aralkyl, or aryl;

provided that when R² is hydrogen and P¹ and P² taken together form an isopropylidene, then R¹ is other than methyl or ethyl.

22. An intermediate having the formula (4) or (4'),

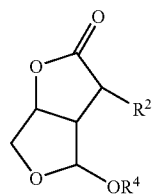
4

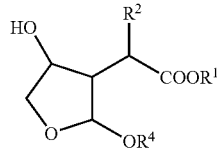
4' wherein R¹ represents alkyl, aryl or aralkyl; R² represents hydrogen or C(=O)OR³; R³ represents alkyl, aryl or aralkyl, or R³, if present, and R¹ taken together with the atoms to which they are attached may form a 6 to 8-membered cyclic group which may be optionally substituted with alkyl, aralkyl, or aryl; OR⁴ represents an alcoholate.

23. An intermediate having the formula (5) or (5'),

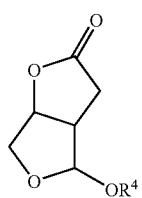
5

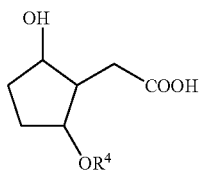
5' wherein OR⁴ represents an alcoholate.

24. An intermediate according to claim 23 wherein the intermediate has the formula (5a)

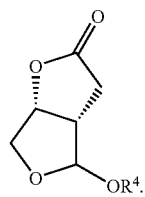
5a

25. An intermediate according to claim 24 in crystalline form.

* * * * *